US008652653B2

(12) United States Patent
Lin et al.

(10) Patent No.: US 8,652,653 B2
(45) Date of Patent: Feb. 18, 2014

(54) HOLE TRANSPORT MATERIALS HAVING A SULFUR-CONTAINING GROUP

(75) Inventors: Chun Lin, Langhorne, PA (US); Bin Ma, WestWindsor, NJ (US); Chuanjun Xia, Lawrenceville, NJ (US); Yonggang Wu, Ewing, NJ (US); Raymond Kwong, Plainsboro, NJ (US)

(73) Assignee: Universal Display Corporation, Ewing, NJ (US)

( * ) Notice: Subject to any disclaimer, the term of this patent is extended or adjusted under 35 U.S.C. 154(b) by 309 days.

(21) Appl. No.: 13/001,577

(22) PCT Filed: Jun. 30, 2009

(86) PCT No.: PCT/US2009/049186
§ 371 (c)(1),
(2), (4) Date: Mar. 16, 2011

(87) PCT Pub. No.: WO2010/002848
PCT Pub. Date: Jan. 7, 2010

(65) Prior Publication Data
US 2011/0163302 A1     Jul. 7, 2011

Related U.S. Application Data

(60) Provisional application No. 61/077,073, filed on Jun. 30, 2008.

(51) Int. Cl.
*H01L 51/54*          (2006.01)

(52) U.S. Cl.
USPC ........... 428/690; 313/504; 313/505; 313/506; 257/40; 257/E51.026; 257/E51.032; 564/26; 564/426; 564/343; 548/304.4; 548/418; 548/440

(58) Field of Classification Search
USPC .................. 428/690, 917; 313/504, 505, 506; 257/40, E51.032, E51.026; 564/26, 564/426, 434; 548/340.4, 418, 440
See application file for complete search history.

(56) References Cited

U.S. PATENT DOCUMENTS

| 4,769,292 A | 9/1988 | Tang et al. |
| 5,247,190 A | 9/1993 | Friend et al. |

(Continued)

FOREIGN PATENT DOCUMENTS

| JP | 2000-299497 | 10/2000 | |
| WO | WO 03/008515 | * 1/2003 | ............. C09K 11/06 |

(Continued)

OTHER PUBLICATIONS

Baldo et al., "Highly Efficient Phosphorescent Emission from Organic Electroluminescent Devices," Nature, vol. 395, 151-154, (1998).

(Continued)

*Primary Examiner* — Gregory Clark
(74) *Attorney, Agent, or Firm* — Duane Morris LLP

(57) ABSTRACT

Novel materials are provided, having a single phenyl or a chain of phenyls where there is a nitrogen atom on each end of the single phenyl or chain of phenyls. The nitrogen atom may be further substituted with particular thiophene, benzothiophene, and triphenylene groups. Organic light-emitting devices are also provided, where the novel materials are used as a hole transport material in the device. Combinations of the hole transport material with specific host materials are also provided.

21 Claims, 3 Drawing Sheets

(56) References Cited

U.S. PATENT DOCUMENTS

| | | | |
|---|---|---|---|
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |
| 6,468,819 | B1 | 10/2002 | Kim et al. |
| 7,279,704 | B2 | 10/2007 | Walters et al. |
| 7,431,968 | B1 | 10/2008 | Shtein et al. |
| 2003/0230980 | A1 | 12/2003 | Forrest et al. |
| 2004/0170863 | A1* | 9/2004 | Kim et al. .................... 428/690 |
| 2004/0174116 | A1 | 9/2004 | Lu et al. |
| 2005/0067951 | A1* | 3/2005 | Richter et al. ................ 313/504 |
| 2007/0088167 | A1 | 4/2007 | Chun et al. |

FOREIGN PATENT DOCUMENTS

| | | |
|---|---|---|
| WO | WO 03/064373 | 8/2003 |
| WO | WO 2010/002848 | 1/2010 |

OTHER PUBLICATIONS

Baldo et al., "Very high-efficiency green organic light-emitting devices based on electrophosphorescence," Appl. Phys. Lett., vol. 75, No. 3, 4-6 (1999).
U.S. Appl. No. 61/077,073, filed Jun. 30, 2008.
U.S. Appl. No. 61/013,391, filed Dec. 28, 2007.
International Search Report issued in PCT/US2009/049186 application.

* cited by examiner (Formula I)

S-5          S-6          S-7

HOLE TRANSPORT MATERIALS HAVING A SULFUR-CONTAINING GROUP

This application is a National Stage of International Application No. PCT/US2009/049186, filed Jun. 30, 2009, which claims priority to U.S. Patent Application No. 61/077,073, filed on Jun. 30, 2008, the disclosures of which are incorporated herein by reference in their entirety.

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to novel materials. More specifically, the present invention relates to novel materials useful in organic light emitting devices (OLEDs).

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the structure:

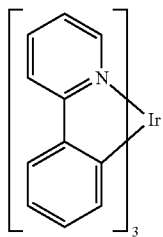

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand is referred to as "photoactive" when it is believed that the ligand contributes to the photoactive properties of an emissive material.

More details on OLEDs, and the definitions described above, can be found in U.S. Pat. No. 7,279,704, which is incorporated herein by reference in its entirety.

SUMMARY OF THE INVENTION

Novel materials are provided, having the chemical structure:

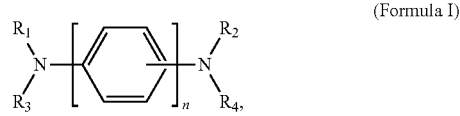

(Formula I)

n is 1, 2 or 3, and the phenyl rings between the nitrogen atoms may be attached to each other and to the nitrogen atoms in a para or meta configuration independently selected for each attachment. Each of $R_1$, $R_2$, $R_3$ and $R_4$ may be independently selected from the group consisting of:

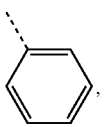

S-1

-continued

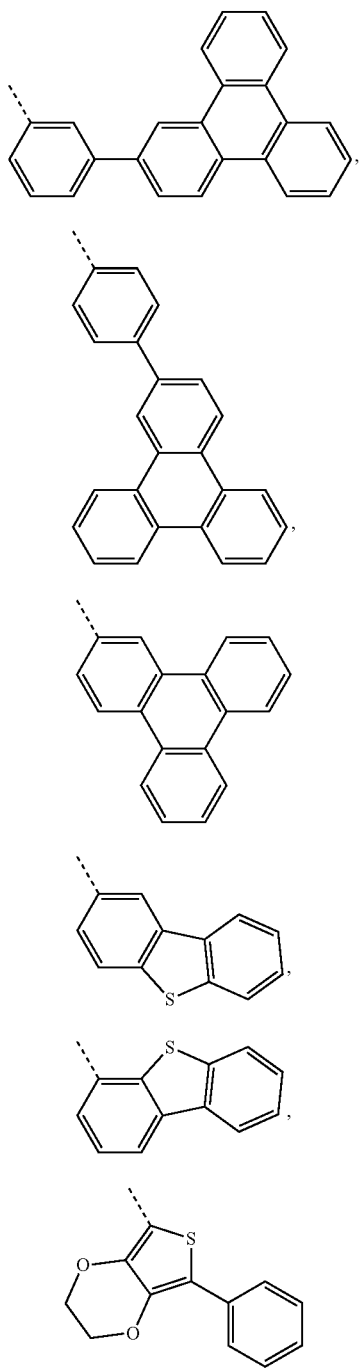

where the dotted line shows the point of attachment to an N atom of Formula I. At least one of $R_1$, $R_2$, $R_3$ and $R_4$ is:

-continued

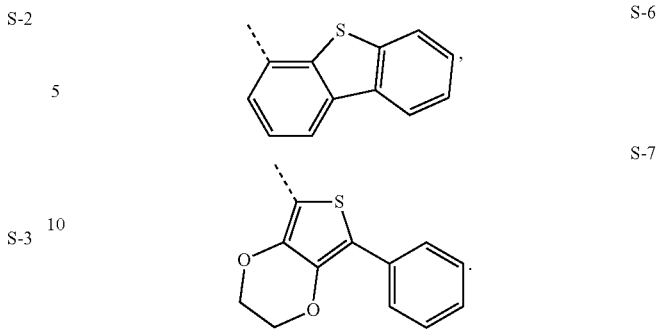

Each of $R_1$, $R_2$, $R_3$ and $R_4$ may be further substituted with substituents that are not fused to $R_1$, $R_2$, $R_3$ and $R_4$. Preferably, at least one of $R_1$, $R_2$, $R_3$, and $R_4$ is S-5. Preferably, at least one of $R_1$, $R_2$, $R_3$, and $R_4$ is S-6. Preferably, at least one of $R_1$, $R_2$, $R_3$, and $R_4$ is S-7. Preferably, both $R_1$ and $R_2$ are S-6.

In one aspect, the materials provided having the chemical structure Formula I more specifically have the structure Formula II.

In another aspect, each of $R_1$, $R_2$, $R_3$, and $R_4$ is independently selected from the group consisting of S-1 and S-5 through S-7.

In yet another aspect, at least one of $R_1$, $R_2$, $R_3$, and $R_4$ is S-8 or S-9. In a further aspect, each of $R_1$, $R_2$, $R_3$, and $R_4$ is independently selected from the group consisting of S-1 and S-5 through S-9.

Specific examples of compositions of matter having Formula I are provided, including materials selected from the group consisting of A-1 through A-6. Preferably, the composition of matter is A-1. Also, specific examples of compositions of matter having Formula I are provided, including materials selected from the group consisting of B-1 through B-6. Preferably, the composition of matter is B-1. Additionally, specific examples of compositions of matter having Formula I are provided, including materials selected from the group consisting of C-1 through C-6. Preferably, the composition of matter is C-1. Moreover, specific examples of compositions of matter having Formula I are provided, including materials selected from the group consisting of D-1 through D-6. Preferably, the composition of matter is D-1.

Organic light-emitting devices and consumer products containing such devices are also provided, where the novel materials are used as a hole transport material in the device. Selections for the compositions of matter having Formula I described as preferred for use in materials having Formula I are also preferred for use in a device or consumer product that includes materials having Formula I. These selections include those described for the substituents $R_1$, $R_2$, $R_3$, and $R_4$, Formula II, and the structures A-1 through A-6, B-1 through B-6, C-1 through C-6, and D-1 through D-6.

Combinations of the hole transport material with specific host materials are also provided. In one aspect, the host is a compound comprising a triphenylene containing benzo-fused thiophene.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
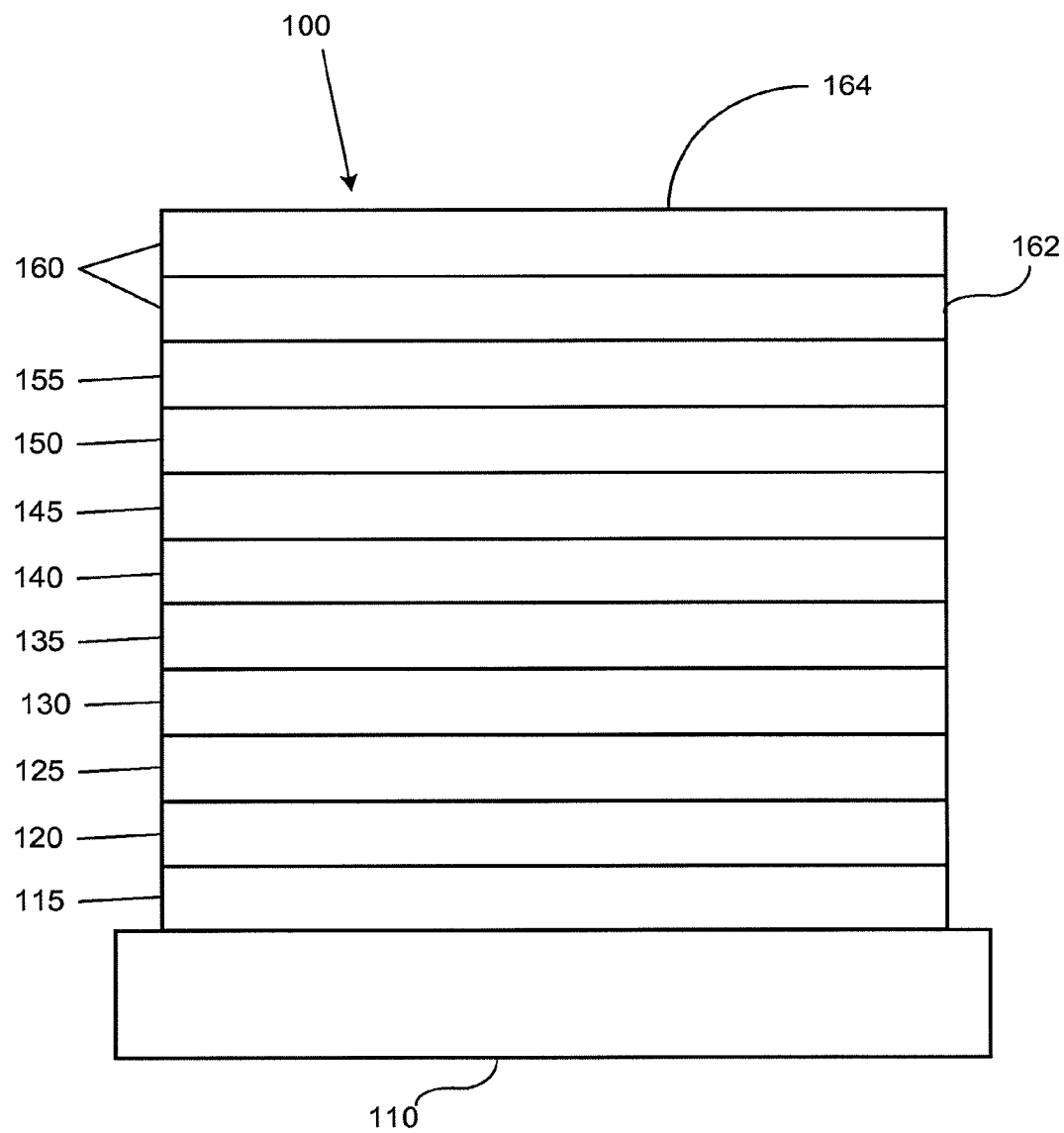
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
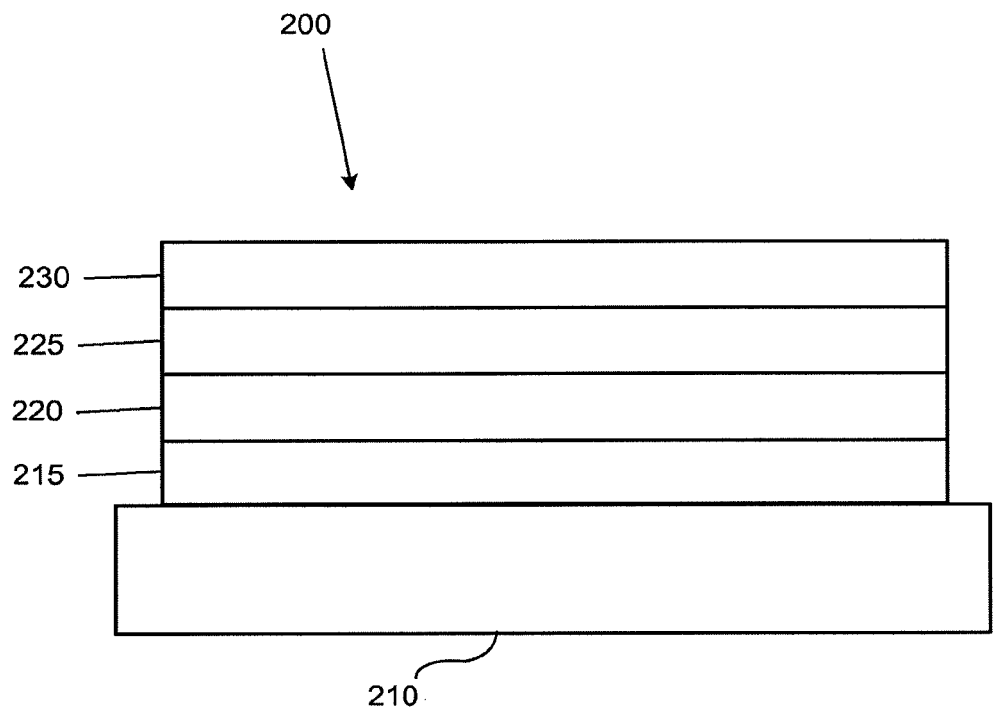
FIG. 2 shows an inverted organic light emitting device that does not have a separate electron transport layer.
Figure 3:
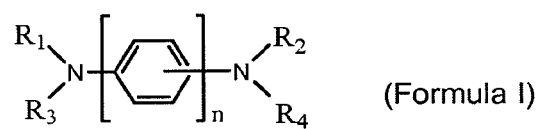
FIG. 3 shows chemical formulae for novel compounds.
Figure 3:
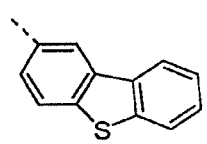
Figure 3:
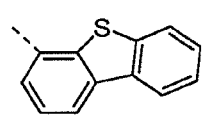
Figure 3:
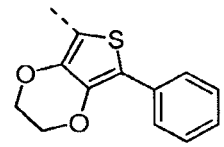

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

A novel composition of matter is provided. The novel composition of matter includes a "core" similar to that of naphthylphenylbiphenyl diamine (α-NPD). As used herein, the core of α-NPD has two nitrogen atoms connected to each other by two phenyl rings, all connected in the para position. Novel compositions of matter are provided having more possibilities for the core, including two nitrogen atoms connected by 1, 2 or 3 phenyl rings, where each connection may independently be para or meta. At least one group attached to a nitrogen atom of the core includes a sulfur containing group. Thus, a novel composition of matter is provided having the structure:

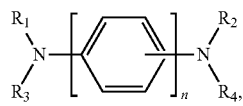

(Formula I)

where n is 1, 2 or 3, and the phenyl rings between the nitrogen atoms may be attached to each other and to the nitrogen atoms in a para or meta configuration independently selected for each attachment. Each of $R_1$, $R_2$, $R_3$ and $R_4$ are independently selected from the group consisting of:

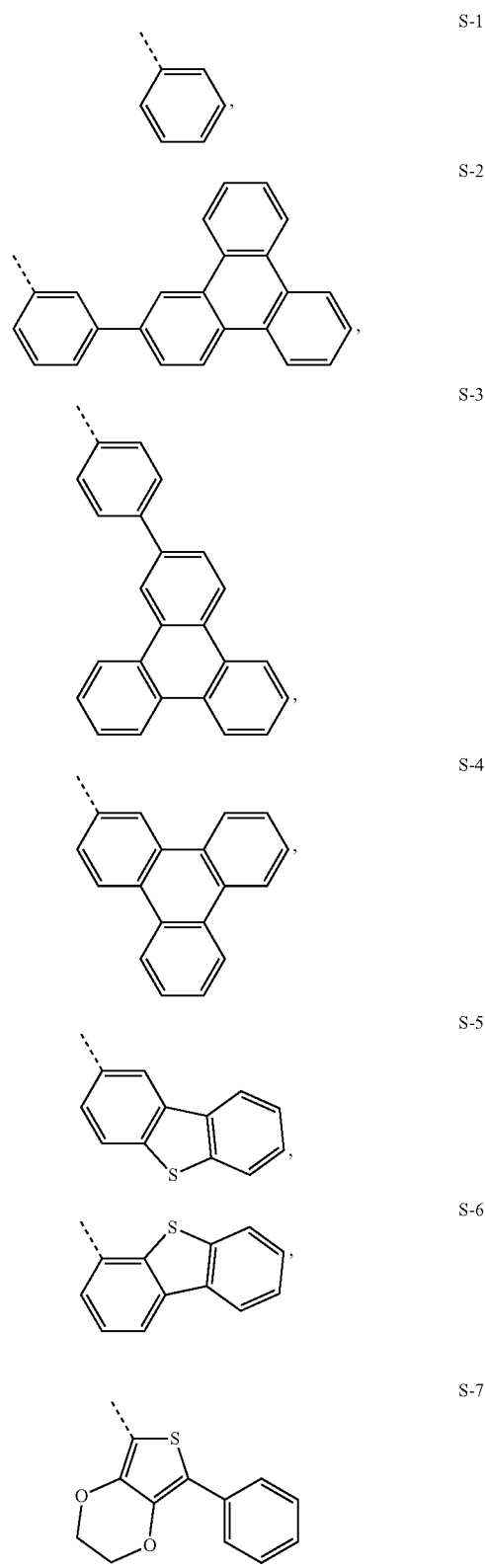

where the dotted line shows the point of attachment to an N atom of Formula I. At least one of $R_1$, $R_2$, $R_3$ and $R_4$ is:

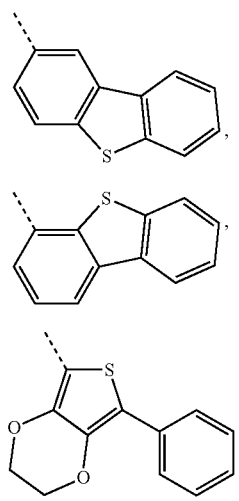

Each of $R_1$, $R_2$, $R_3$ and $R_4$ may be further substituted with substituents that are not fused to $R_1$, $R_2$, $R_3$ and $R_4$.

Without being limited to any theory as to why the novel materials are desirable, it is believed that the benzidine (4,4'-diaminobiphenyl) core, along with the variations described herein, are particularly desirable. Benzidine with one phenyl and one 1-naphthyl attached to each of the nitrogens is α-NPD and is a widely used hole transport layer in OLEDs. However, α-NPD does not work well in certain devices, particularly blue and green devices, which have higher energy triplets and charge carriers. It is believed that the napthyl group of α-NPD, in connection with high energy charge carriers and triplets, may be responsible for this instability, and that a sulfur containing group as disclosed herein in Groups A-D, preferably dibenzothiophene (DBT), has superior stability in this context.

Hole transport materials incorporating dibenzothiophene group may have more efficiency and/or longer lived than devices incorporating other groups, such as biphenyl, naphthalene. It is believed that the following two points are important factors for HTL in phosphorescent device stability: 1) HTL should not only have good hole (oxidation) stability while transporting holes, but also should have good electron (reduction) stability; 2) HTL should have higher triplet energy than dopants in its adjacent emissive layer to prevent it from quenching caused by the exciton migration. Dibenzothiophene is a conjugated compound with reversible reduction (by solution electrochemistry), indicating that it may be a stable electron carrier. In addition, dibenzothiophene itself has much higher triplet energy (414 nm) than many other organic molecules, such as biphenyl, naphthalene. The enhanced stability and efficiency of dibenzothiophene-containing HTL may be attributed to a combination of the above effects. This may lead to the devices using the HTL materials described herein have higher stability and efficiency than devices using conventional HTL such as α-NPD.

Hole transport materials incorporating 3,4-ethylenedioxythiophene (EDOT) group may also be desirable such as higher hole conductivity hence low device voltage. Poly(3,4-ethylenedioxythiophene) (PEDOT) is a very important conducting polymer. Its complex with poly(styrene sulfonic acid) has been widely used for antistatic coatings and hole injection layer for polymer OLEDs. The oxyethane bridge across the 3,4 positions of the monomer makes the thiophene very electron rich, therefore sufficient HOMO raising is effected and polymerization is forced to occur through the open 2,5-positions yielding a linear, highly conjugated polymer. The oxidized form of the polymer is highly stable under ambient conditions. The redox property of the film does not change over a long period of time. It is desired to incorporate the EDOT building block into a triarylamine HTL (e.g., benzidine) scaffold to improve the redox properties of the hole injection/transporting materials. The direct linkage of EDOT to nitrogen will raise the HOMO of the molecule and therefore make it better aligned with the ITO interface.

It is preferred that the sulfur containing group of Group A-D is directly attached to a nitrogen of the core. It is believed that such direct attachment maintains a higher triplet energy for the molecule, which is desirable in many situations.

Preferably, at least one of $R_1$ and $R_3$, and at least one of $R_2$ and $R_4$, is a group that includes a sulfur-containing group from one of the groups A-D. While molecules having a sulfur-containing group attached to only one nitrogen of the core are useable, it is believed that molecules having at least one sulfur containing group attached to each nitrogen of the core results in a more stable molecule. It is also believed that adding additional sulfur containing groups after there is at least one attached to each nitrogen may not result in much further improvement. While it is generally easier to use only one type of sulfur-containing group in a molecule, possible multiple times, different sulfur-containing groups may also be used in the same molecule.

The core of α-NPD is preferred, where the part of the composition represented by Formula I is more specifically:

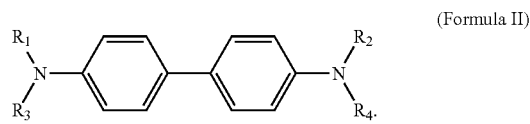

Molecules where each of $R_1$, $R_2$, $R_3$ and $R_4$ are independently selected from the group consisting of:

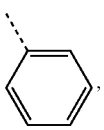

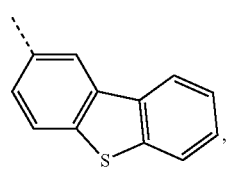

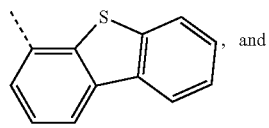

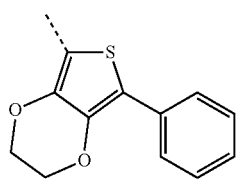
S-7

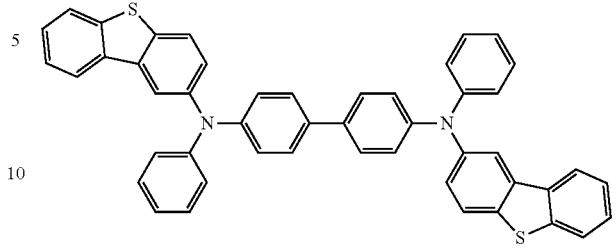
A-1 may be preferred. Such molecules include at least one sulfur-containing group per one of Groups A-D, and any substituents that are not such groups are a phenyl, which should not strongly affect the electronic properties imparted to the molecule by the sulfur-containing group. The following substituents may be used for reasons similar to phenyl:

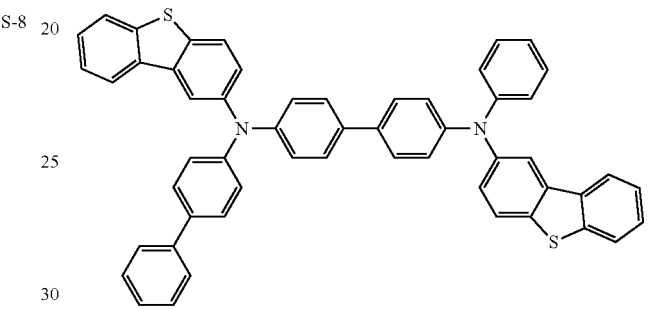
A-2

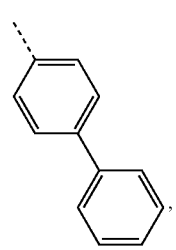
S-8

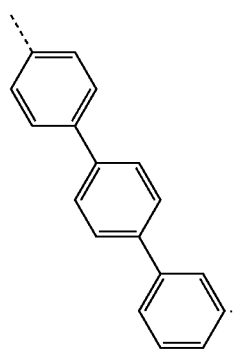
S-9

A-3

Molecules including each of the sulfur-containing groups of Groups A-D disclosed herein may be preferred, depending upon the context.

A composition of matter where at least one of $R_1$, $R_2$, $R_3$ and $R_4$ is

A-4

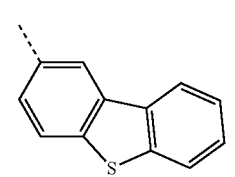
S-5 may be preferred. These compounds may be referred to as being in the A-group of compounds. Non-limiting examples of specific preferred molecules including this substituent include:

A-5
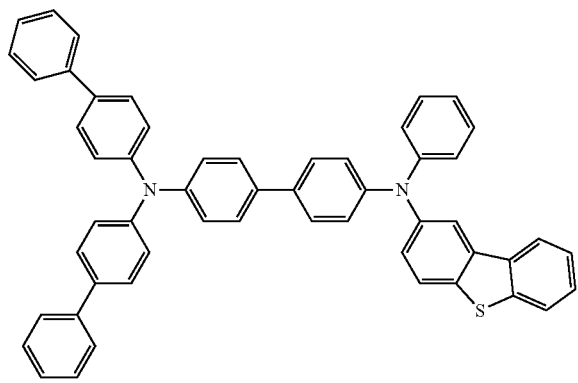
A-6
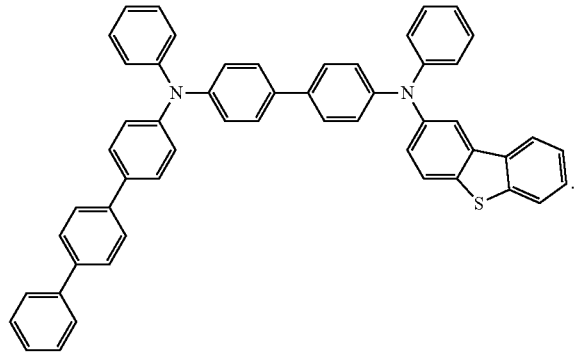
A composition of matter where at least one of $R_1$, $R_2$, $R_3$ and $R_4$ is
S-6
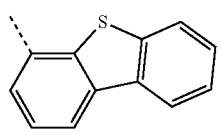
may be preferred. These compounds may be referred to as being in the B-group of compounds. Non-limiting examples of specific preferred molecules including this substituent include:
B-1
B-2
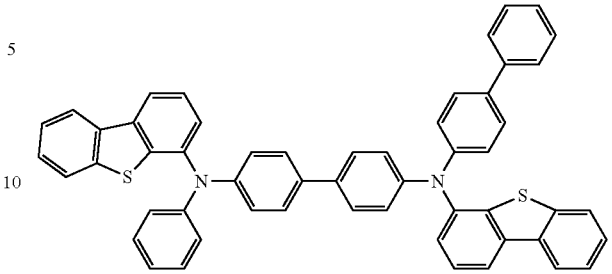
B-3
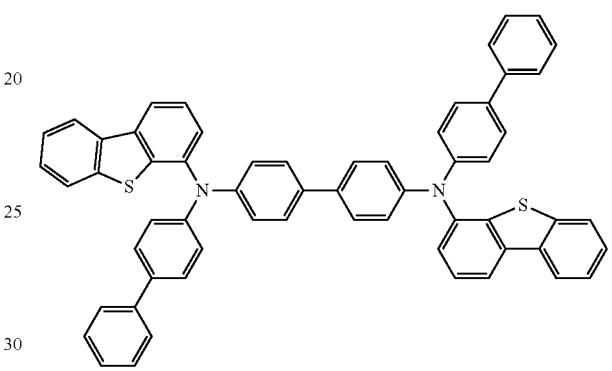
B-4
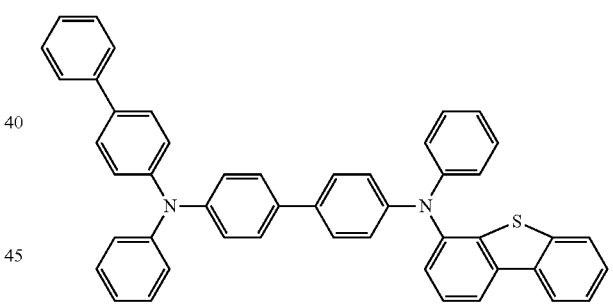
B-5
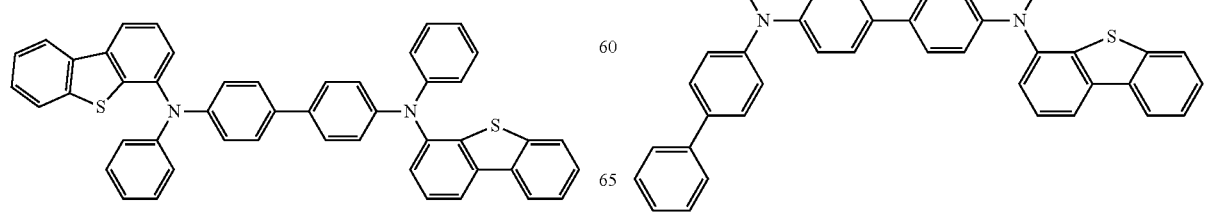

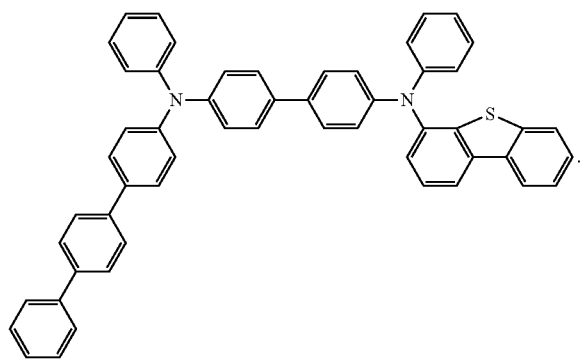
B-6
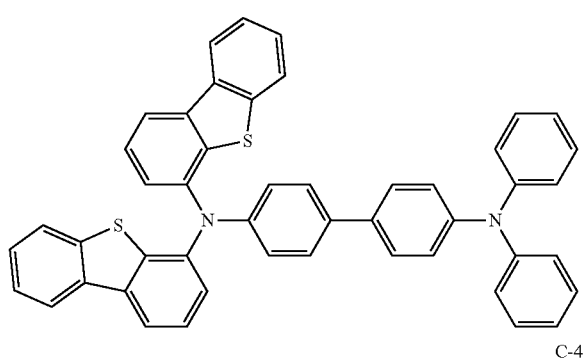
C-3
A composition of matter where both $R_1$ and $R_2$ are
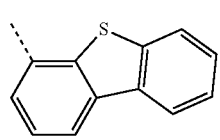
S-6
may be preferred. These compounds may be referred to as being in the C-group of compounds. The C-group of compounds is a subset of the B-group of compounds. Non-limiting examples of specific preferred molecules including this substituent include:
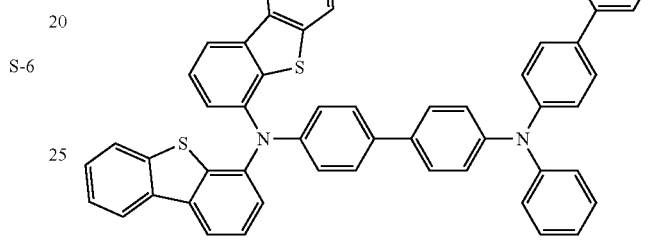
C-4
C-1
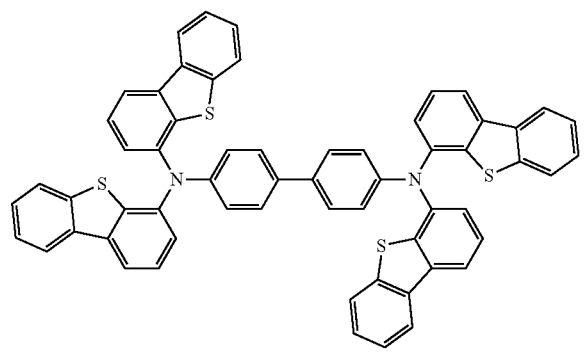
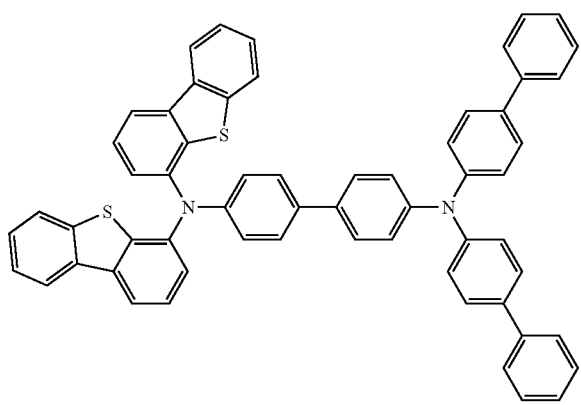
C-5
C-2
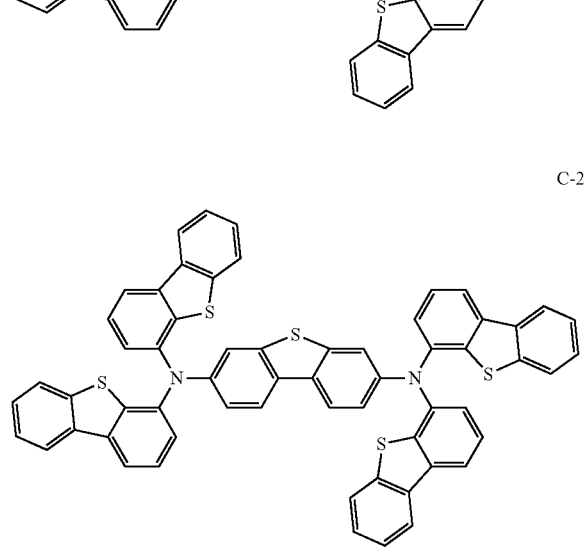
C-6

A composition of matter where at least one of $R_1$, $R_2$, $R_3$ and $R_4$ is

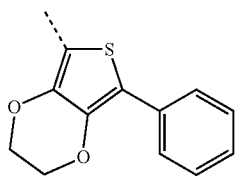

S-7 may be preferred. These compounds may be referred to as being in the D-group of compounds. Non-limiting examples of specific preferred molecules including this substituent include:

D-1

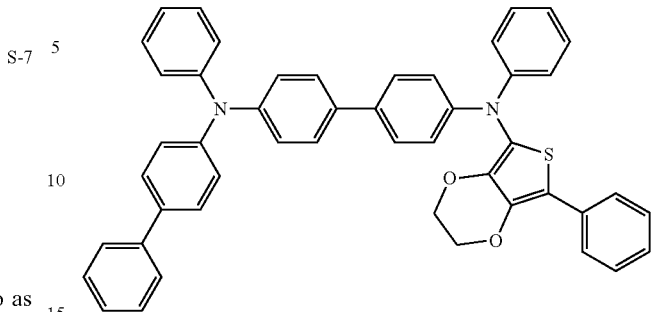

D-4

D-2

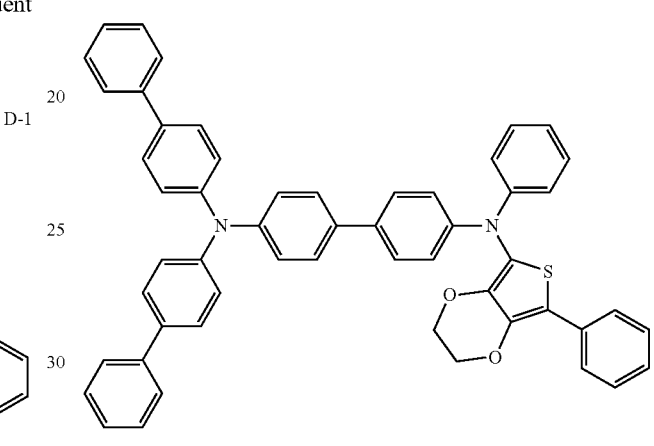

D-5

D-3

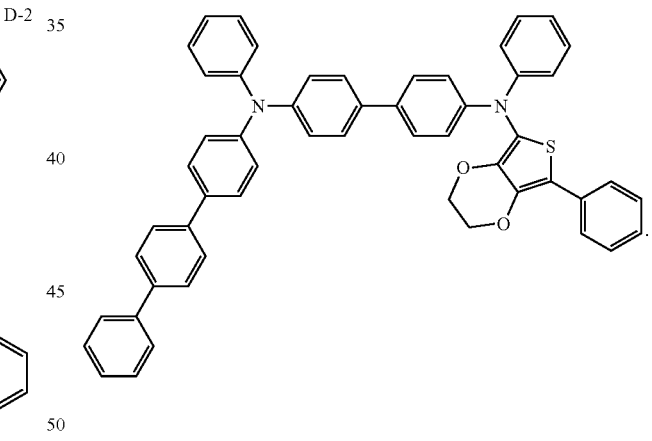

D-6

For the R groups that are do not include a sulfur containing group from one of groups A-D, the following structures are preferred:

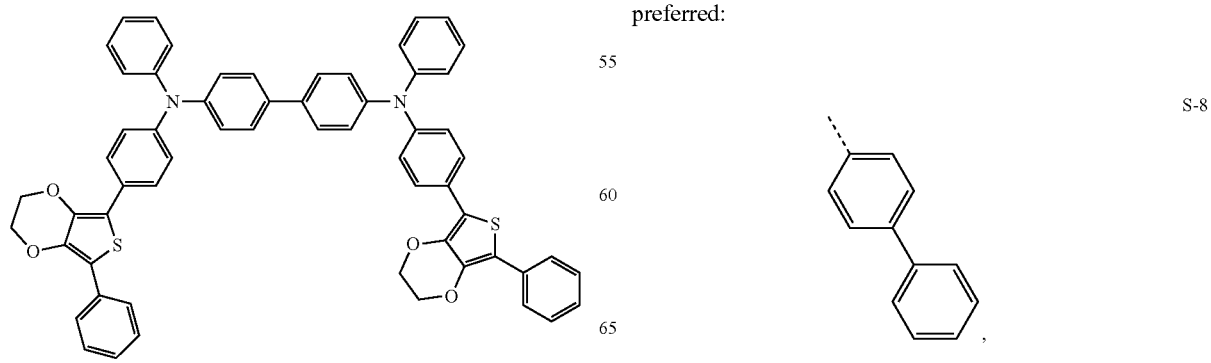

S-8

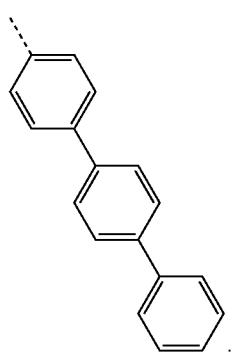
A composition of matter of Formula I is preferred where each of $R_1$, $R_2$, $R_3$ and $R_4$ is independently selected from the group consisting of:
S-1
S-2
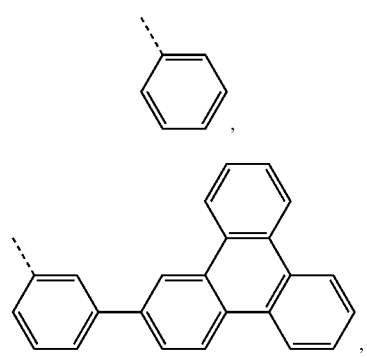
S-3
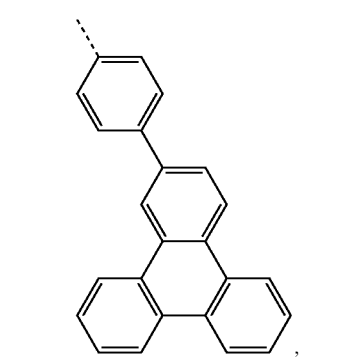
S-4
S-5
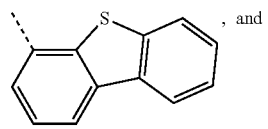
, and
S-6
S-7
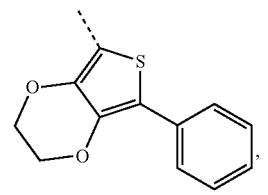
S-8
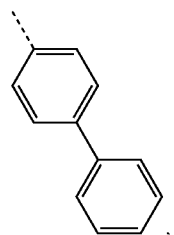
S-9
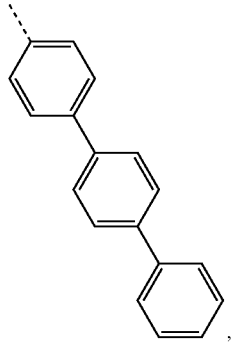
at least one of $R_1$, $R_2$, $R_3$ and $R_4$ is selected from the group consisting of:
S-5
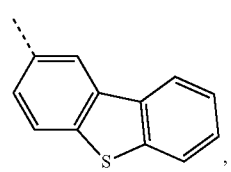
S-6
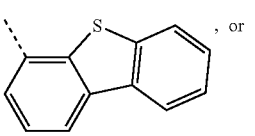
, or
S-7
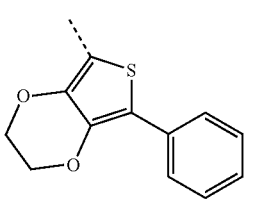
and there are no further substitutions to $R_1$, $R_2$, $R_3$ and $R_4$.

A composition of matter of Formula I is preferred where each of $R_1$, $R_2$, $R_3$ and $R_4$ is independently selected from the group consisting of:

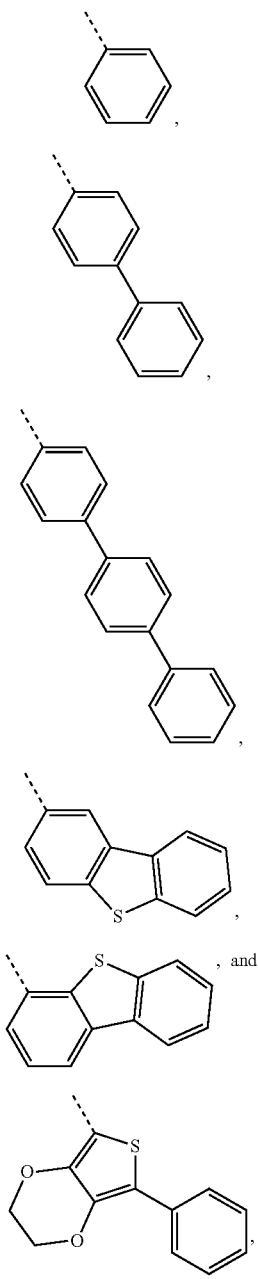

at least one of $R_1$, $R_2$, $R_3$ and $R_4$ is selected from the group consisting of:

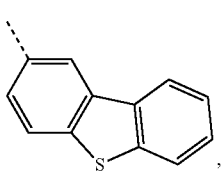

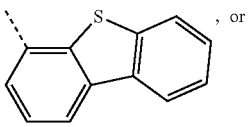

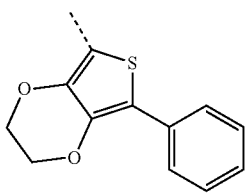

and there are no further substitutions to $R_1$, $R_2$, $R_3$ and $R_4$.

Molecules A-1, B-1, C-1 and D-1 have been synthesized, and a description of the synthesis is provided. The other molecules in the A, B, C and D groups of molecules, and the variations to those molecules described herein, can be readily fabricated using similar chemical synthesis.

An organic light emitting device is also provided. The device may include an anode, a cathode, and an organic emissive layer disposed between the anode and the cathode. The organic emissive layer may includes a host and a phosphorescent dopant. The device may also include an organic hole transport layer comprising a hole transport material, disposed between the organic emissive layer and the anode, and in direct contact with the organic emissive layer. The hole transport layer may have the structure of the novel compositions of matter disclosed herein, i.e., the structure of the novel materials having a core consistent with Formula I. The phosphorescent dopant is preferably an organo-metallic iridium material.

In addition, consumer products wherein the consumer product includes an organic light emitting device including a composition of matter having the structure of Formula I, as described, are provided. Selections for the substituents and structures described as preferred for the compositions of matter having the structure Formula I are also preferred for the devices and the consumer products including devices that comprise a composition of matter having the structure of Formula I. These selections include those described for substituents $R_1$, $R_2$, $R_3$, and $R_4$, Formula II, and structures A-1 through A-6, B-1 through B-6, C-1 through C-6, and D-1 through D-6.

Organic light emitting devices having at least one of $R_1$, $R_2$, $R_3$ and $R_4$ being:

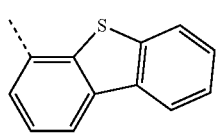

were fabricated. Specifically, molecule B-1 was used to fabricate devices, and it is believed that other molecules as disclosed herein having the same sulfur containing group would have similar performance. The devices had particularly good performance.

It is believed that the compounds having a sulfur containing group disclosed herein, when used as a hole transport layer, work particularly well in devices where the host is a compound comprising a triphenylene containing benzo-fused thiophene. Such hosts are disclosed in U.S. Patent Application 61/013,391, filed Dec. 28, 2007, inventor Ma, Bin, which is incorporated herein by reference in its entirety and particularly for claimed subject matter. Compound 2 is an example of such a host. The B group of materials are preferred hole transport materials for this combination.

It is believed that sulfur containing hole transport materials described herein are desirable for use in fluorescent OLEDs in addition to phosphorescent OLEDs.

As used herein, the following compounds have the following structures:

Compound 1—disclosed in JP 2000-299497:

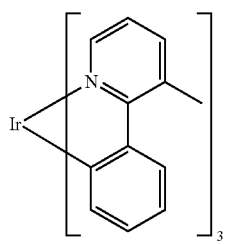

Compound 1

Compound 2—disclosed in U.S. Patent Application 61/013, 391, filed Dec. 28, 2007, inventor Ma, Bin.

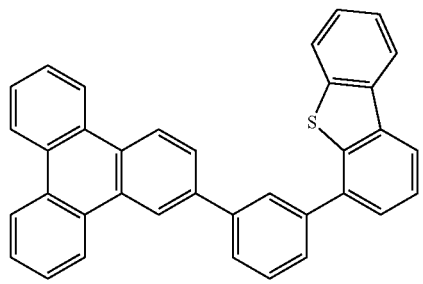

Compound 2

Bis(2-methyl-8-hydroxyquinolinolato)(4-phenylphenolato) aluminum (BAlq) and tris-(8-hydroxyquinolato) aluminum (Alq$_3$) are well known materials. LG-101 and LG-201 are proprietary materials available for purchase from LG Chem, Inc. of Korea.

EXPERIMENTAL

Synthesis of A-1

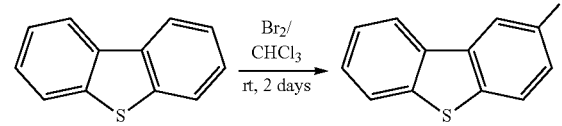

Synthesis of 2-bromodibenzothiophene

Dibenzothiophene (15 g, 79.9 mmol) was dissolved in 1.5 L chloroform. To the solution, bromine (12.76 g, 79.9 mmol) was added dropwise. The reaction mixture was vigorously stirring for 2 days at room temperature and then treated with sodium sulfite water solution. The organic phase was evaporated to give a white solid which has 48% unreacted dibenzothiophene, 50% 2-bromodibenbzothiophene and less 2% 2,8-dibromodibenzothiophene based on GC-MS and HPLC results. The mixture was repeatedly recrystallized with ethyl acetate to get pure 2-bromodibenzothiophene.

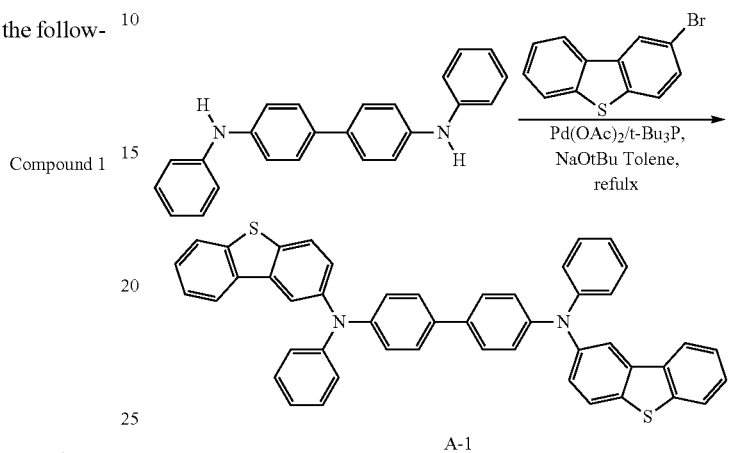

A-1

Synthesis of A-1

2-bromodibenzothiophene (9.19 mmol), diamine (1.45 g, 4.18 mmol), Pd(OAc)$_2$ (30 mg, 0.125 mmol), 1 M t-Butyphosphine in toluene (0.25 mL, 0.25 mmol), t-BuONa (1.3 g, 12.8 mmol) and 150 mL toluene were charged in a 250 mL round bottle flask. The reaction mixture was heated up to reflux for overnight under nitrogen. Reaction mixture was cooled down and was separated with silica gel column to get ~2.6 g (89%) product which was confirmed by proton NMR.

Synthesis of B-1

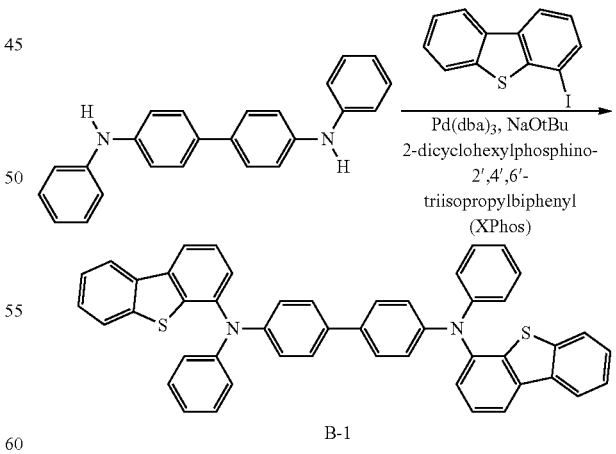

B-1

To a 500 mL round flask was added N,N'-Diphenylbenzidine (2.4 g, 7 mmol), 4-iododibenzothiophene (5.6 g, 18 mmol), Pd$_2$(dba)$_3$ (0.2 g, 0.2 mmol), 2-dicyclohexylphosphino-2',4',6'-triisopropylbiphenyl (XPhos, 0.4 g, 0.8 mmol), sodium t-butoxide (2.9 g, 30 mmol), and 150 mL of toluene. The reaction was heated to reflux and stirred under a nitrogen

Synthesis of C-1

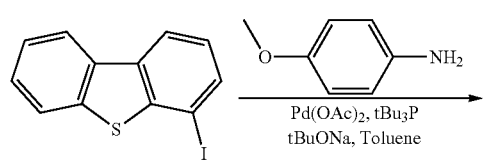

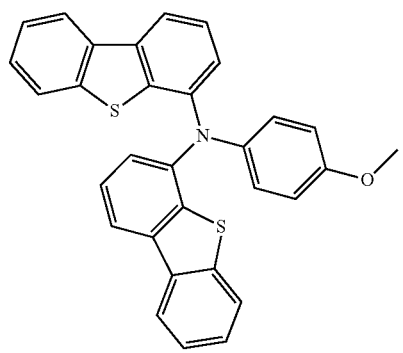

Synthesis of N-(dibenzo[b,d]thiophen-4-yl)-N-(4-methoxyphenyl)dibenzo[b,d]thiophen-4-amine palladium acetate (0.07 g, 0.33 mmol) and 1.0 M tri(t-butyl)phosphine solution in toluene (0.67 mL, 0.67 mmol) were added to a three-neck flask under nitrogen. 150 mL of toluene was then added. The solution was stirred under nitrogen until the color disappeared. To the solution was added 4-iododibenzothiophene (7.4 g, 24 mmol), sodium tert-butoxide (3.3 g, 33 mmol), and 4-methoxyaniline (1.4 g, 11 mmol) in sequence. The mixture was then heated up to reflux for 4 h. After cooled to room temperature, the mixture was filtered through a silica gel plug. The product was purified by column chromatography using 30% of dichloromethane in hexanes as eluent. 4.6 g of desired product was obtained after purification. (85% yield)

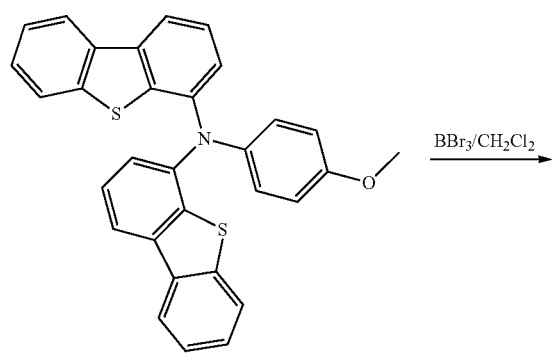

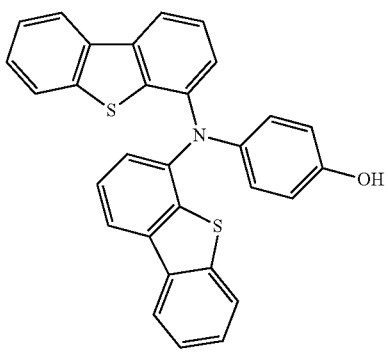

Synthesis of 4-(bis(dibenzo[b,d]thiophen-4-yl)amino)phenol

N-(dibenzo[b,d]thiophen-4-yl)-N-(4-methoxyphenyl)dibenzo[b,d]thiophen-4-amine (4.6 g, 9.4 mmol) was dissolved in 100 mL of anhydrous dichloromethane. The solution was cooled with a dry ice/isopropanol bath. To the solution was added boron tribromide solution in hexanes (1.0 M solution, 16 mL). The reaction was allowed to warm to room temperature for 6 h. The reaction was quenched with water. The product was purified with column chromatography using dichloromethane as eluent. 4 g of desired product was obtained. (90% yield)

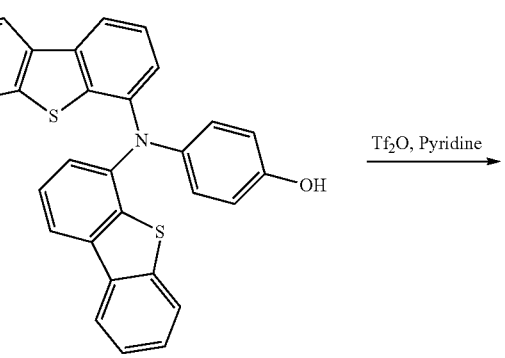

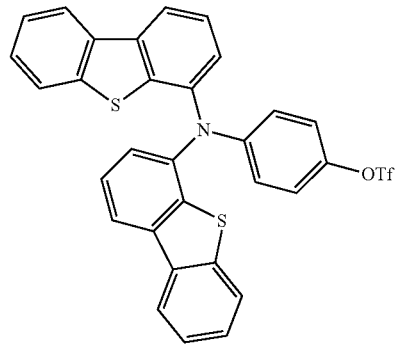

Synthesis of 4-(bis(dibenzo[b,d]thiophen-4-yl)amino)phenyl trifluoro-methanesulfonate 4-(bis(dibenzo[b,d]thiophen-4-yl)amino)phenol (4.0 g, 8.4 mmol) was dissolved in 60 mL of anhydrous dichloromethane. The solution was cooled with an ice-water bath. To the solution was added pyridine (1.7 mL, 21 mmol) and then triflic anhydride (1.7 mL, 10.1 mmol). The reaction was stirred for 20 minutes and then quenched with water. The organic layer was separated. The solvent was evaporated under reduced pressure. The residue was purified by column chromatography using 1:3 dichloromethane and hexanes as eluent. 4.15 g of desired product was obtained. (82%

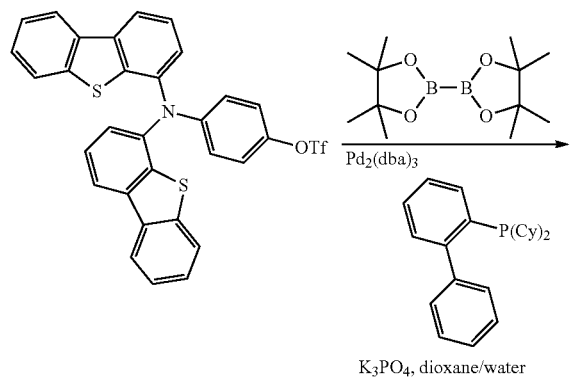

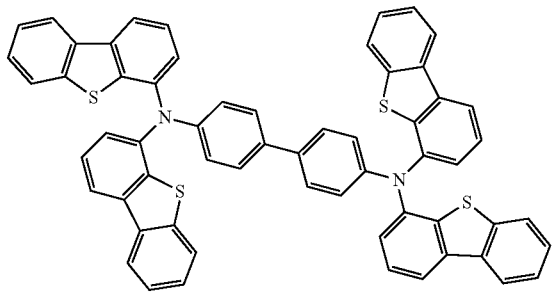

C-1

Synthesis of C-1, $N^4,N^4,N^{4'},N^{4'}$-tetrakis(dibenzo[b,d]thiophen-4-yl)biphenyl-4,4'-diamine 4-(bis(dibenzo[b,d]thiophen-4-yl)amino)phenyl trifluoromethanesulfonate (4.0 g, 6.6 mmol), bispinacolatodiboron (0.84 g, 3.3 mmol), biphenyl-2-yldicyclohexylphosphine (0.09 g, 0.26 mmol), potassium phosphate (3.5 g, 16.5 mmol) were added to a three-neck flask. 100 mL of dioxane and 5 mL of water was then added. The mixture was purged with nitrogen for 30 minutes. $Pd_2(dba)_3$ (0.06 g, 0.07 mmol) was added. The reaction mixture was heated to 60° C. for 4 h. The reaction mixture was filtered through a magnesium sulfate bed. The solvent was then evaporated. The residue was dissolved in dichloromethane and then precipitated from isopropanol. The solid was collected by filtration. The product was further purified by column using 1:2 to 1:1 of dichloromethane and hexanes as eluent. 2 g of desired product was obtained.

Synthesis of D-1

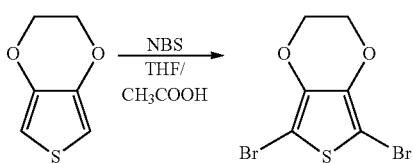

Synthesis of 2,5-dibromo-3,4-ethylene dioxythiophene 3,4-ethylene dioxythiophene (EDOT) (5 g, 35 mmol) was dissolved in the mixture of 70 mL THF and 70 mL acetic acid. NBS (13.2 g, 74 mmol) was slowly added into the solution. The reaction was stirred at room temperature for 2 h, then 350 mL water was added. The precipitation was collected by filtration and washed with water. The collected silver grey solid was dried in a desiccator with applied vacuum overnight and gave 10.3 gram 2,5-dibromo-3,4-ethylene dioxythiophene (33 mmol, yield 94.6%).

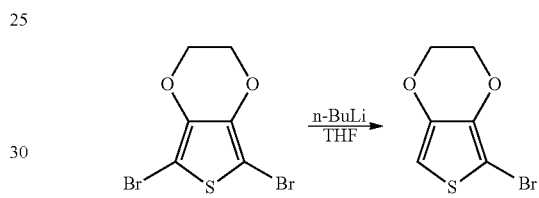

Synthesis of 2-bromo-3,4-ethylene dioxythiophene 2,5-dibromo-EDOT (10.3 g, 33 mmol) was dissolved in 200 mL anhydrous THF and cooled to −78° C. by acetone/dry ice bath. Then 22.1 mL n-BuLi (1.6 M in hexane) was added dropwise into the solution. After warmed to room temperature, the reaction was quenched by 170 mL HCl (1 M) and extracted with methylene chloride (200 mL×2). The combined organic layer was dried over $MgSO_4$ and concentrated by rotovap to get 10.5 gram brown liquid, which was used directly for next step without further purification and without drying to constant weight.

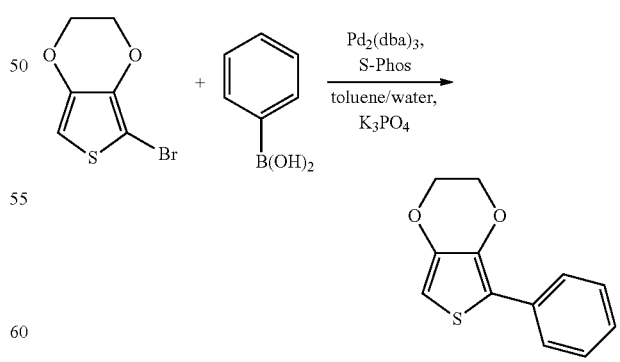

Synthesis of 2-phenyl-3,4-ethylene dioxythiophene

The mixture of 2-bromo-EDOT (10.5 g, 47 mmol), phenylboronic acid (8.1 g, 66 mmol), potassium phosphate tribasic (30 g, 142.5 mmol), 300 mL toluene and 30 mL water was prepared. Nitrogen was bubbled directly in the mixture for 15 minutes. Then tris(dibenzylideneacetone)dipalladium (435 mg, 0.48 mmol) and S-Phos (788 mg, 1.92 mmol) were added. The nitrogen was bubbled in the mixture for another 15 minutes. The reaction mixture was refluxed overnight under nitrogen. The next day the reaction mixture was cooled to room temperature. The organic layer was separated and the aqueous layer was extracted by dichloromethane. The combined organic layers were dried over magnesium sulfate, filtered and concentrated under reduced pressure. The resulted black oil was distilled by Kugelrohr at 160° C. to get rid of the black color. Then another distillation by Kugelrohr at 100° C. successfully got rid of the impurities. The 6 gram (27.5 mmol, total yield of last two steps: 83%) light yellow oil left in the original flask was used for next step without further purification.

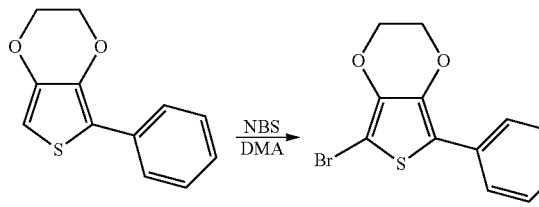

Synthesis of 2-bromo-5-phenyl-3,4-ethylene dioxythiophene 2-phenyl-EDOT (6 g, 28 mmol) was dissolved in DMA and cooled to 0° C. by ice bath and was bubbled with nitrogen. NBS (5.4 g, 30.2 mmol) was dissolved in 35 mL DMA and added dropwise into the 2-phenyl-EDOT solution under nitrogen. After all NBS was added, the reaction was warmed to room temperature and stirred for 20 minutes. The mixture then was poured into ice water, extracted by dichloromethane. The combined organic layer was dried over magnesium sulfate, filtered and concentrated by rotovap and Kugelrohr. The red solid was recrystallized from hot methanol to get 5.7 gram grey solid (19 mmol, 70% yield).

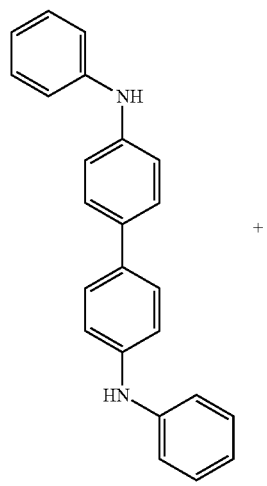

-continued

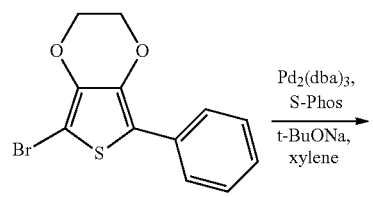

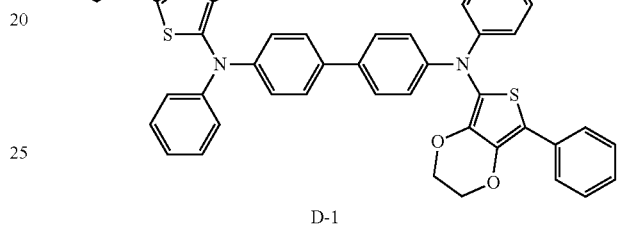

D-1

Synthesis of D-1

A mixture of 2-bromo-5-phenyl-EDOT (2 g, 6.7 mmol), diphenylbenzidine (0.57 g, 1.68 mmol), t-BuONa (0.48 g, 5.04 mmol) and xylene (80 mL) was prepared. Nitrogen was bubbled directly in the mixture for 15 minutes. Next was added tris(dibenzylideneacetone)dipalladium (23 mg, 1.5% equivalent) and S-Phos (41 mg, 6% equivalent) then the nitrogen was bubbled in the mixture for another 20 minutes. The reaction mixture was refluxed overnight under nitrogen. The next day the reaction mixture was cooled to room temperature, then was filter through a celite plug and washed out with dichloromethane. The filtration was concentrated and purified by column (15% EtOAc in hexanes first, then washed with the solvent of 30% EtOAc and 10% dichloromethane in hexanes). The resulted yellow solid was recrystallized from hot dichloromethane and methanol to give 0.7 g (0.5 mmol, yield 30%) yellow solid.

Devices

Devices were fabricated using standard techniques. The devices have structures similar to that shown in FIG. 1, but including the specific layers and materials described in the table.

TABLE 1

Structures of green PHOLEDs with novel HTL materials and novel host/HTL combinations vs comparative examples.

| Example | HIL | HTL | Host | Compound 1, % | BL | ETL |
|---|---|---|---|---|---|---|
| 1 | LG-101 300 Å | α-NPD 100 Å | Compound 2 | 10% | Compound 2 100 Å | LG-201 300 Å |
| 2 | LG-101 300 Å | B-1 100 Å | Compound 2 | 10% | Compound 2 100 Å | LG-201 300 Å |
| 3 | LG-101 300 Å | α-NPD 100 Å | Compound 2 | 10% | Compound 2 100 Å | Alq 400 Å |
| 4 | LG-101 300 Å | B-1 100 Å | Compound 2 | 10% | Compound 2 100 Å | Alq 400 Å |

TABLE 2

Performance of green PHOLEDs with novel HTL materials and novel host/HTL combinations vs. comparative examples.

| | CIE | | Voltage | LE | EQE | PE | At 1,000 nits $LT_{50\%}$ | Lo | At 40 mA/cm² $LT_{80\%}[h]$ | |
|---|---|---|---|---|---|---|---|---|---|---|
| Example | x | y | [V] | [cd/A] | [%] | [lm/W] | [h] | [nits] | RT | 70° C. |
| 1 | 0.351 | 0.608 | 5.6 | 49.1 | 13.5 | 27.5 | 204,995 | 14,624 | 349 | 65 |
| 2 | 0.347 | 0.612 | 5.6 | 57.7 | 15.9 | 23.4 | | 18,163 | 340 | |
| 3 | 0.351 | 0.612 | 5.8 | 53.5 | 14.7 | 29.0 | 213,955 | 16,084 | 372 | |
| 4 | 0.350 | 0.613 | 5.7 | 62.1 | 17.1 | 34.2 | | 19,540 | 265 | |

2 groups of experiments are shown in tables 1 and 2. The superior performance of green PHOLED devices with novel HTL material B-1 is shown relative to devices having an NPD HTL. The desirability of combining HTL materials similar to B-1 with hosts similar to Compound 2 is also shown.

Group 1

Examples 1 and 2

The difference between Example 1 (comparative) and Example 2 is that Example 1 has an α-NPD HTL, whereas Example 2 has an HTL of Compound B-1. The combination of HTL B-1 with Compound 2 as a host gives results superior to a similar device using an α-NPD HTL. Example 2 shows superior performance in efficiency and the lifetime. Moreover, the results for Example 2 are particularly good for a green-emitting device in general, showing the desirability of combining HTLs with compounds similar to B-1 with hosts similar to Compound 2.

Group 2

Examples 3 and 4

Group 2 makes a similar comparison to that made in Group 1, except using an ETL of Alq instead of LG-201. The same conclusions can be drawn from Group 2 as from Group 1.

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 3 below. Table 3 lists non-limiting classes of materials, non-limiting examples of compounds for each class, and references that disclose the materials.

TABLE 3

| MATERIAL | EXAMPLES OF MATERIAL | PUBLICATIONS |
|---|---|---|
| Hole injection materials | | |
| Phthalocyanine and porphryin compounds | 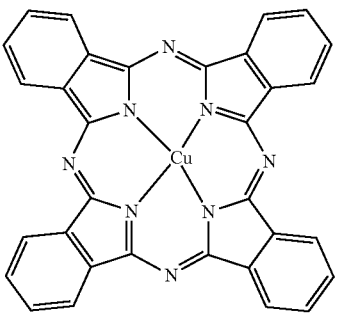 | Appl. Phys. Lett. 69, 2160 (1996) |
| Starburst triarylamines | 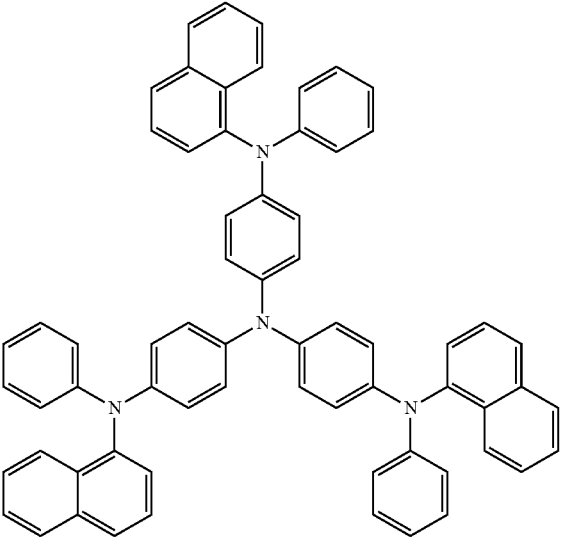 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |
| $CF_x$ Fluorohydrocarbon polymer | $-[CH_xF_y]_n-$ | Appl. Phys. Lett. 78, 673 (2001) |
| Conducting polymers (e.g., PEDOT:PSS, polyaniline, polypthiophene) | 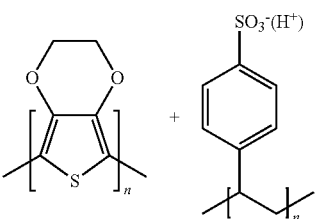 | Synth. Met. 87, 171 (1997) |
| Arylamines complexed with metal oxides such as molybdenum and tungsten oxides | 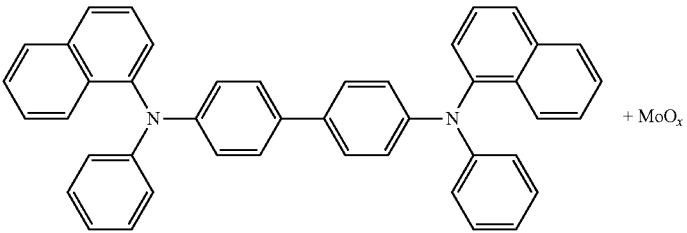 [SMILES: c1ccc(N(c2ccc(-c3ccc(N(c4ccccc4)c4cccc5ccccc45)cc3)cc2)c2cccc3ccccc23)cc1] + $MoO_x$ | SID Symposium Digest, 37, 923 (2006) |

TABLE 3-continued
| MATERIAL | EXAMPLES OF MATERIAL | PUBLICATIONS |
|---|---|---|
| Hole transporting materials | | |
| Triarylamines (e.g., TPD, α-NPD) | 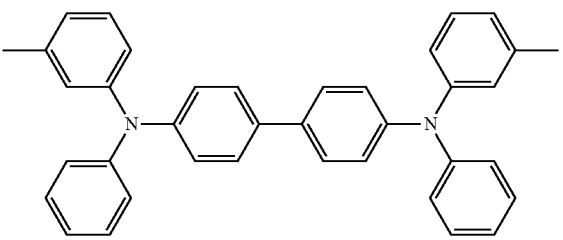 | Appl. Phys. Lett. 51, 913 (1987) |
| | 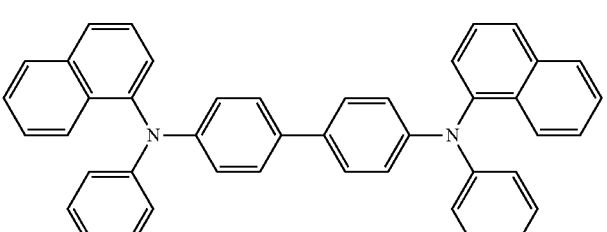 | US5061569 |
| | 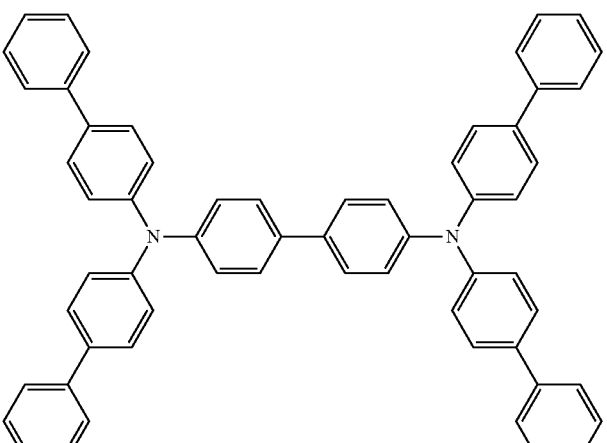 | EP650955 |
| | 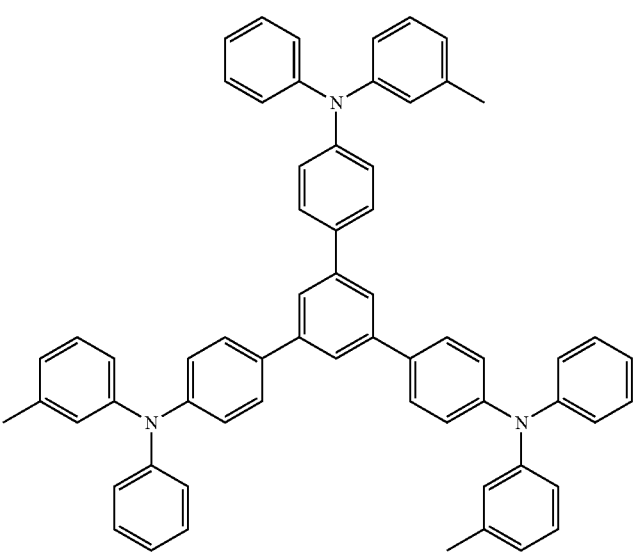 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |

TABLE 3-continued
| MATERIAL | EXAMPLES OF MATERIAL | PUBLICATIONS |
|---|---|---|
| | 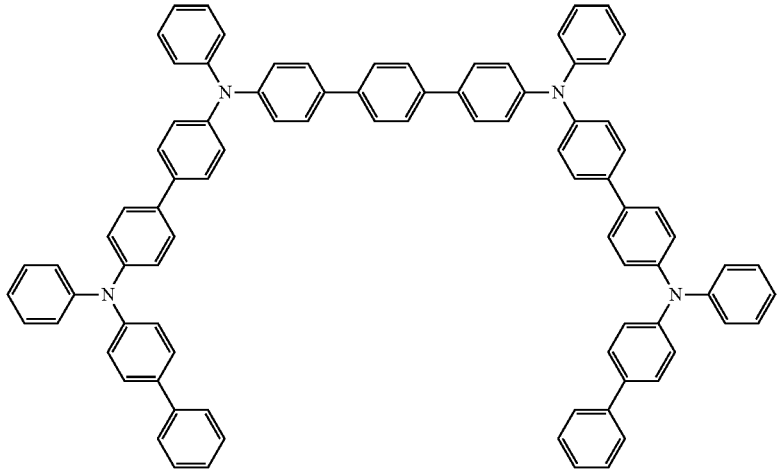 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |
| | 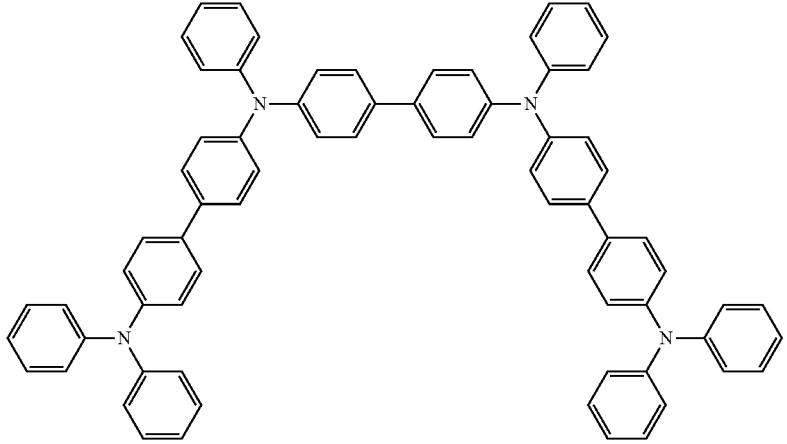 [SMILES: c1ccc(N(c2ccccc2)c2ccc(-c3ccc(N(c4ccccc4)c4ccc(-c5ccc(N(c6ccccc6)c6ccc(-c7ccc(N(c8ccccc8)c8ccccc8)cc7)cc6)cc5)cc4)cc3)cc2)cc1] | Appl. Phys. Lett. 90, 183503 (2007) |
| Triaylamine on spirofluorene core | 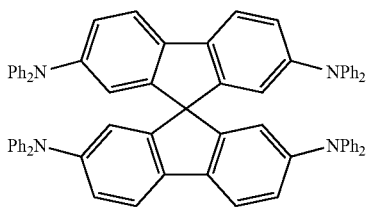 | Synth. Met. 91, 209 (1997) |

TABLE 3-continued
| MATERIAL | EXAMPLES OF MATERIAL | PUBLICATIONS |
|---|---|---|
| Arylamine carbazole compounds | 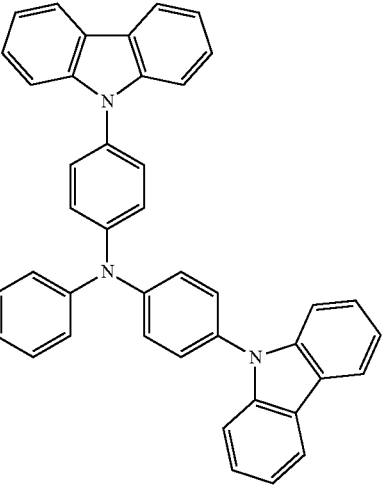 | Adv. Mater. 6, 677 (1994) |
| Indolocarbazoles | 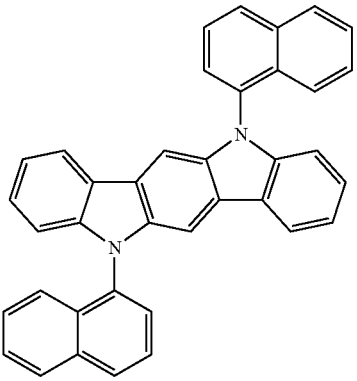 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 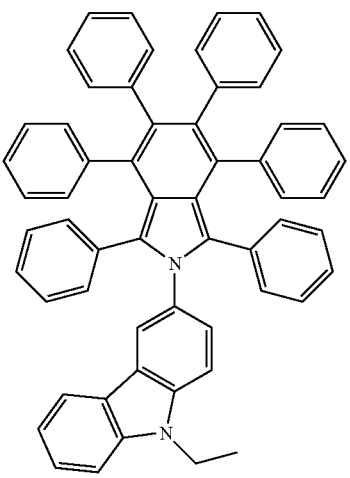 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
Phosphorescent OLED host materials
Red hosts TABLE 3-continued
| MATERIAL | EXAMPLES OF MATERIAL | PUBLICATIONS |
|---|---|---|
| Arylcarbazoles | 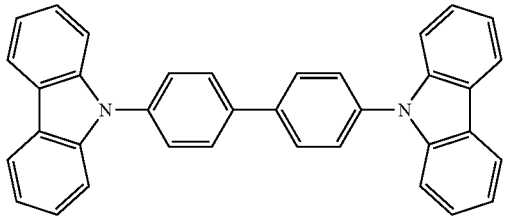 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| Metal 8-hydroxyquinolates (e.g., Alq$_3$, BAlq) | 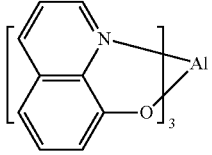 | Nature 395, 151 (1998) |
| | 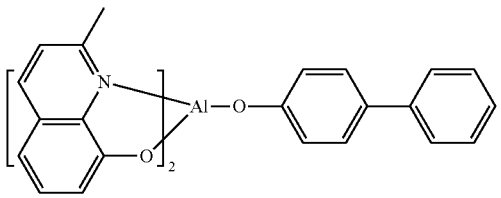 | US20060202194 |
| | 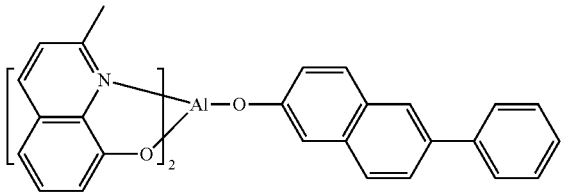 | WO2005014551 |
| Metal phenoxybenzothiazole compounds | 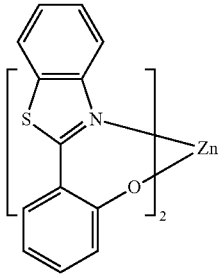 | Appl. Phys. Lett. 90, 123509 (2007) |
| Conjugated oligomers and polymers (e.g., polyfluorene) | 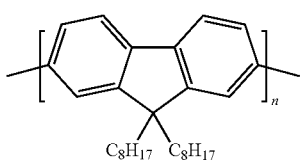 | Org. Electron. 1, 15 (2000) |
| Green hosts | | |
| Arylcarbazoles | 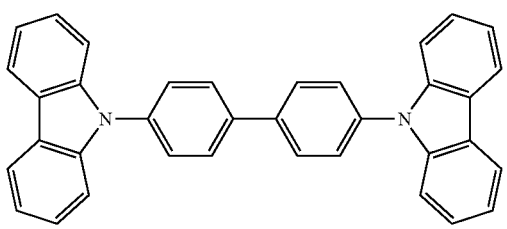 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |

TABLE 3-continued
| MATERIAL | EXAMPLES OF MATERIAL | PUBLICATIONS |
|---|---|---|
| | 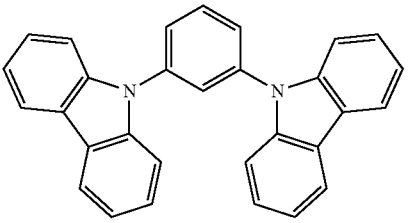 [SMILES: c1cc(-n2c3ccccc3c3ccccc32)cc(-n2c3ccccc3c3ccccc32)c1] | US2003175553 |
| | 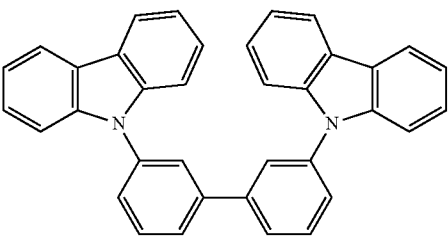 [SMILES: c1cc(-c2cccc(-n3c4ccccc4c4ccccc43)c2)cc(-n2c3ccccc3c3ccccc32)c1] | WO2001039234 |
| Aryltriphenylene compounds | 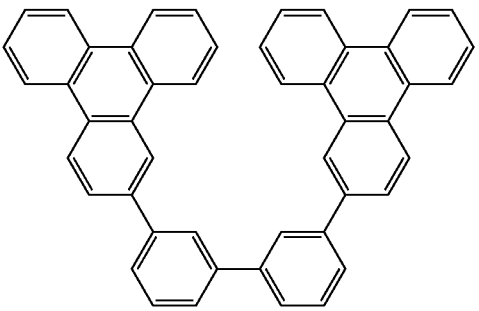 [SMILES: c1cc(-c2cccc(-c3ccc4c5ccccc5c5ccccc5c4c3)c2)cc(-c2ccc3c4ccccc4c4ccccc4c3c2)c1] | US20060280965 |
| | 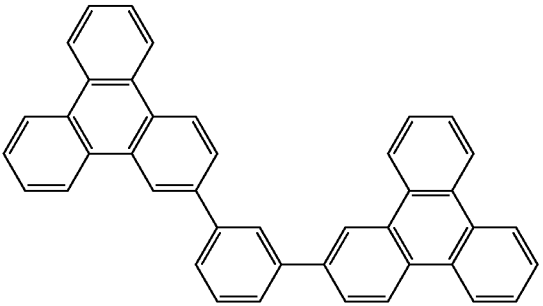 [SMILES: c1cc(-c2ccc3c4ccccc4c4ccccc4c3c2)cc(-c2ccc3c4ccccc4c4ccccc4c3c2)c1] | US20060280965 |
| Polymers (e.g., PVK) | 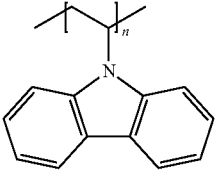 | Appl. Phys. Lett. 77, 2280 (2000) |
| Spirofluorene compounds | 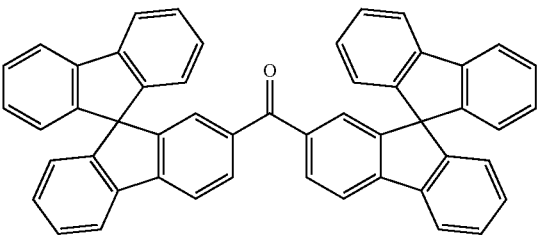 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |

TABLE 3-continued

| MATERIAL | EXAMPLES OF MATERIAL | PUBLICATIONS |
| --- | --- | --- |
| Metal phenoxybenzooxazole compounds | | WO05089025 |
| | | WO06132173 |
| | | JP200511610 |
| Spirofluorene-carbazole compounds | | JP2007254297 |
| | | JP2007254297 |

TABLE 3-continued

| MATERIAL | EXAMPLES OF MATERIAL | PUBLICATIONS |
| --- | --- | --- |
| Indolocabazoles | | WO07063796 |
| | | WO07063754 |
| 5-member ring electron deficient heterocycles (e.g., triazole, oxadiazole) | | J. Appl. Phys. 90, 5048 (2001) |
| | | WO04107822 |
| Metal phenoxypyridine compounds | | WO05030900 |
| Blue hosts | | |
| Arylcarbazoles | | Appl. Phys. Lett, 82, 2422 (2003) |

TABLE 3-continued

| MATERIAL | EXAMPLES OF MATERIAL | PUBLICATIONS |
| --- | --- | --- |
| | | US20070190359 |
| Dibenzothiophene-carbazole compounds | | WO2006114966 |
| Phosphorescent dopants | | |
| Red dopants | | |
| Heavy metal porphyrins (e.g., PtOEP) | | Nature 395, 151 (1998) |
| Iridium(III) organometallic complexes | | Appl. Phys. Lett. 78, 1622 (2001) |
| | | US06835469 |

TABLE 3-continued

| MATERIAL | EXAMPLES OF MATERIAL | PUBLICATIONS |
| --- | --- | --- |
| | | US06835469 |
| | | US20060202194 |
| | | US20060202194 |
| | | US07087321 |
| | | US07087321 |

TABLE 3-continued

| MATERIAL | EXAMPLES OF MATERIAL | PUBLICATIONS |
| --- | --- | --- |
| | [Ir complex with isoquinoline ligand bearing $C_8H_{17}$ substituent, tris form] | Adv. Mater. 19, 739 (2007) |
| Platinum(II) organometallic complexes | [Pt complex with isoquinolinyl-phenyl and acetylacetonate ligands] | WO2003040257 |
| Osminum(III) complexes | [Os(PPhMe$_2$)$_2$ complex with CF$_3$-pyrazolyl-pyridine ligand] | Chem. Mater. 17, 3532 (2005) |
| Ruthenium(II) complexes | [Ru(PPhMe$_2$)$_2$ complex with $^t$Bu-pyrazolyl-isoquinoline ligand] | Adv. Mater. 17, 1059 (2005) |
| Green dopants | | |
| Iridium(III) organometallic complexes | [Ir(ppy)$_3$ structure]<br>and its derivatives | Inorg. Chem. 40, 1704 (2001) |

TABLE 3-continued
| MATERIAL | EXAMPLES OF MATERIAL | PUBLICATIONS |
|---|---|---|
| | 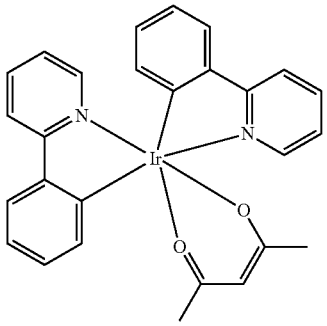 | US2002034656 |
| | 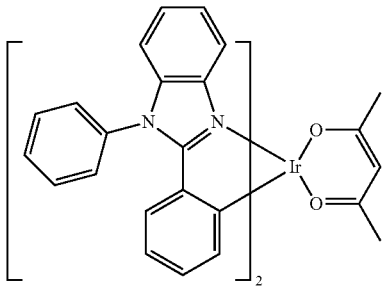 | US06687266 |
| | 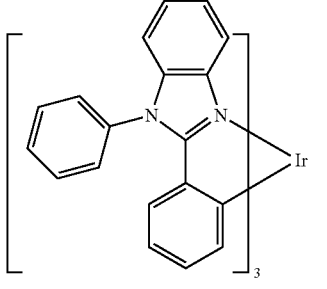 | Chem. Mater. 16, 2480 (2004) |
| | 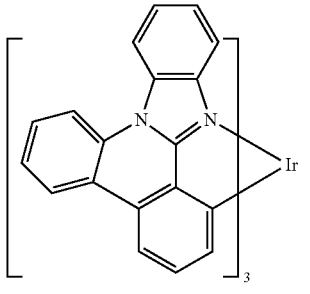 | US2007190359 |
| | 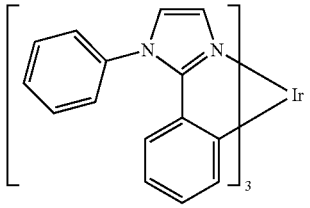 | US 2006008670<br>JP2007123392 |

TABLE 3-continued

| MATERIAL | EXAMPLES OF MATERIAL | PUBLICATIONS |
|---|---|---|
| | | Adv. Mater. 16, 2003 (2004) |
| | | Angew. Chem. Int. Ed. 2006, 45, 7800 |
| Pt(II) organometallic complexes | | Appl. Phys. Lett. 86, 153505 (2005) |
| | | Appl. Phys. Lett. 86, 153505 (2005) |
| | | Chem. Lett. 34, 592 (2005) |

TABLE 3-continued

| MATERIAL | EXAMPLES OF MATERIAL | PUBLICATIONS |
| --- | --- | --- |
| Gold complexes | | Chem. Commun. 2906 (2005) |
| Rhenium(III) complexes | | Inorg. Chem. 42, 1248 (2003) |
| Blue dopants | | |
| Iridium(III) organometallic complexes | | WO2002002714 |
| | | WO2006009024 |
| | | US2006251923 |
| | | WO2006056418, US2005260441 |

TABLE 3-continued

| MATERIAL | EXAMPLES OF MATERIAL | PUBLICATIONS |
|---|---|---|
| | | US2007190359 |
| | | US2002134984 |
| | | Angew. Chem. Int. Ed. 47, 1 (2008) |
| | | Chem. Mater. 18, 5119 (2006) |
| | | Inorg. Chem. 46, 4308 (2007) |
| | | WO05123873 |

TABLE 3-continued
| MATERIAL | EXAMPLES OF MATERIAL | PUBLICATIONS |
|---|---|---|
| | 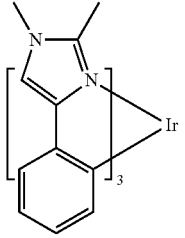 | WO05123873 |
| | 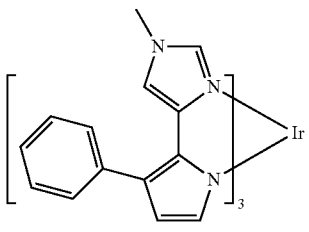 | WO07004380 |
| | 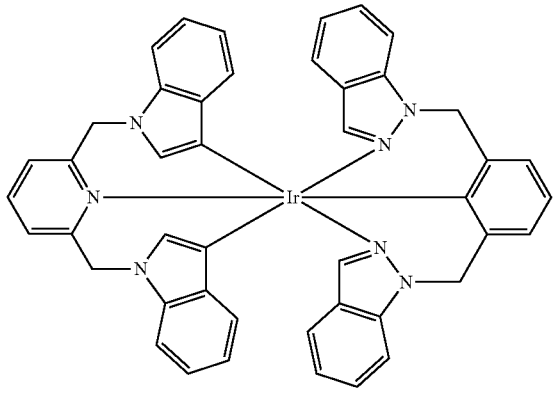 | WO06082742 |
| Osmium(II) complexes | 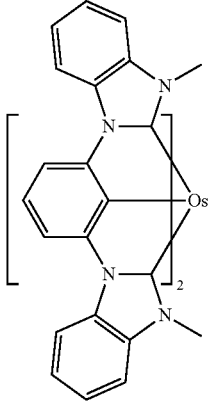 | US2005260449 |
| | 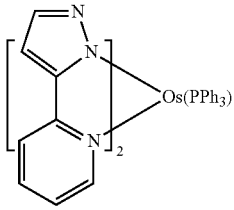 | Organometallics 23, 3745 (2004) |

TABLE 3-continued

| MATERIAL | EXAMPLES OF MATERIAL | PUBLICATIONS |
| --- | --- | --- |
| Gold complexes | | Appl. Phys. Lett. 74, 1361 (1999) |
| Platinum(II) complexes | | WO06098120, WO06103874 |
| Exciton/hole blocking layer materials | | |
| Bathocuprine compounds (e.g., BCP, BPhen) | | Appl. Phys. Lett. 75, 4 (1999) |
| | | Appl. Phys. Lett. 79, 449 (2001) |
| Metal 8-hydroxyquinolates (e.g., BAlq) | | Appl. Phys. Lett. 81, 162 (2002) |
| 5-member ring electron deficient heterocycles such as triazole, oxadiazole, imidazole, benzoimidazole | | Appl. Phys. Lett. 81, 162 (2002) |

TABLE 3-continued
| MATERIAL | EXAMPLES OF MATERIAL | PUBLICATIONS |
|---|---|---|
| Triphenylene compounds | 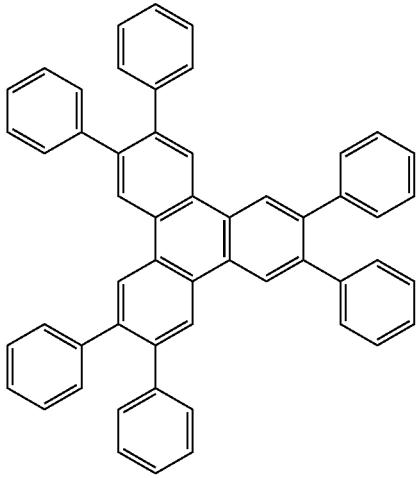 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 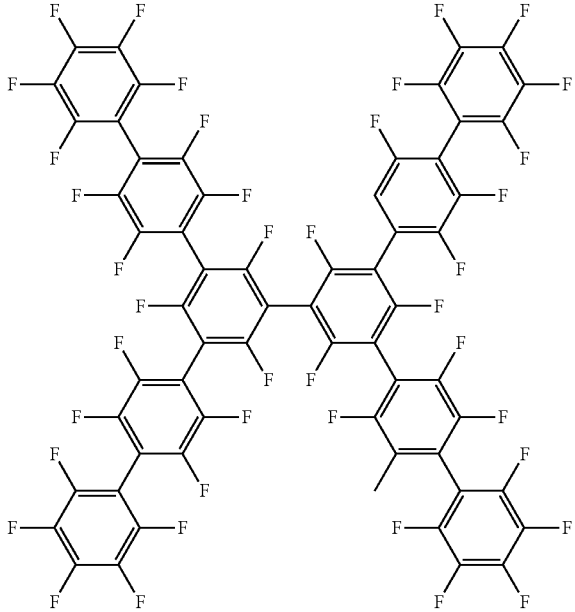 [SMILES: Cc1c(F)c(-c2c(F)c(-c3cc(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
Electron transporting materials TABLE 3-continued

| MATERIAL | EXAMPLES OF MATERIAL | PUBLICATIONS |
|---|---|---|
| Anthracene-benzoimidazole compounds | | WO03060956 |
| Anthracene-benzothiazole compounds | | Appl. Phys. Lett. 89, 063504 (2006) |
| Metal 8-hydroxyquinolates (e.g., Alq$_3$) | | Appl. Phys. Lett. 51, 913 (1987) |
| Metal hydroxybenoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |

TABLE 3-continued
| MATERIAL | EXAMPLES OF MATERIAL | PUBLICATIONS |
|---|---|---|
| 5-member ring electron deficient heterocycles (e.g., triazole, oxadiazole, imidazole, benzoimidazole) | 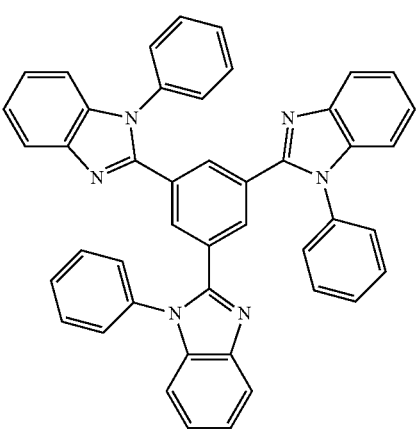 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |
| | 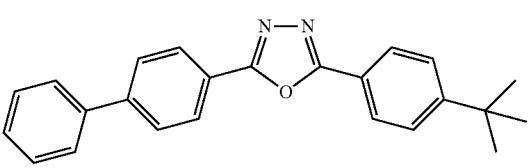 [SMILES: CC(C)(C)c1ccc(-c2nnc(-c3ccc(-c4ccccc4)cc3)o2)cc1] | Appl. Phys. Lett. 55, 1489 (1989) |
| | 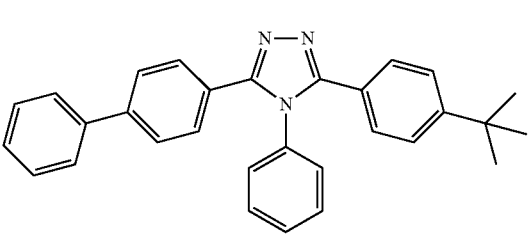 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 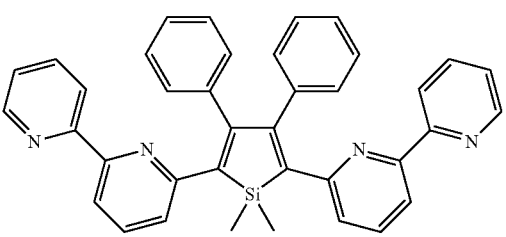 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 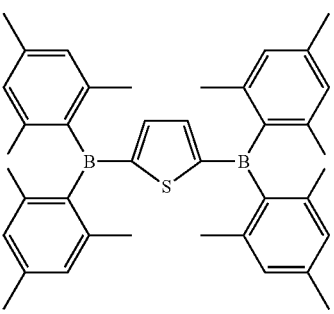 [SMILES: Cc1cc(C)c(B(c2ccc(B(c3c(C)cc(C)cc3C)c3c(C)cc(C)cc3C)s2)c2c(C)cc(C)cc2C)c(C)c1] | J. Am. Chem. Soc. 120, 9714 (1998) |
| Fluorinated aromatic compounds | 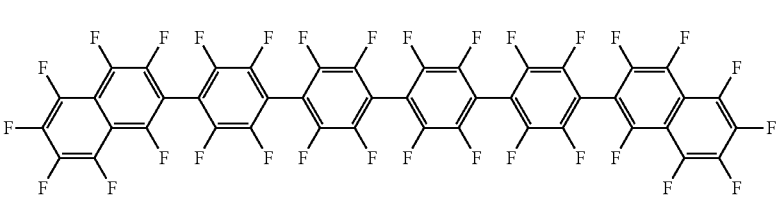 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. It is understood that various theories as to why the invention works are not intended to be limiting.

The invention claimed is:

1. A composition of matter having the chemical structure:

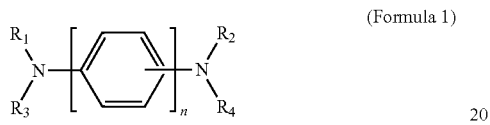

(Formula 1)

wherein n is 1, 2 or 3, and the phenyl rings between the nitrogen atoms may be attached to each other and to the nitrogen atoms in a para or meta configuration independently selected for each attachment;

wherein each of $R_2$, $R_3$ and $R_4$ are independently selected from the group consisting of:

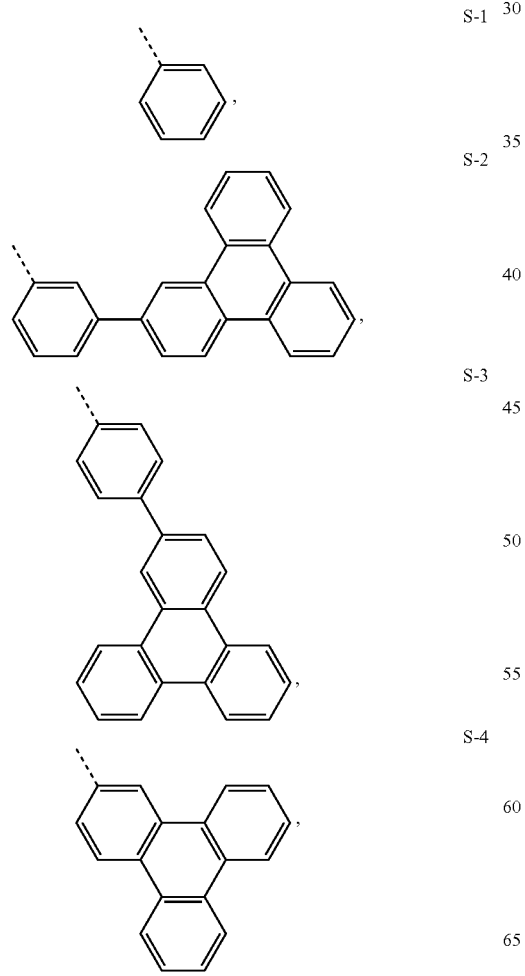

S-1,
S-2,
S-3,
S-4,

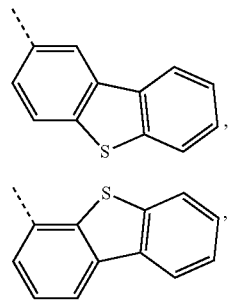

S-5,
S-6,

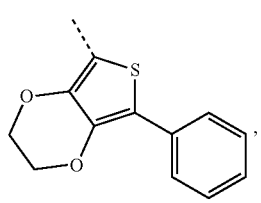

S-7,

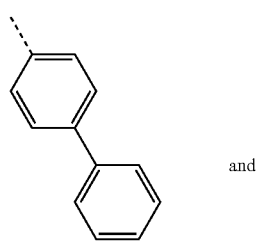

S-8, and

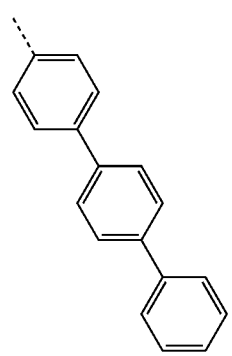

S-9, wherein $R_1$ is selected from the group consisting of:

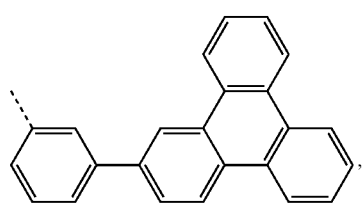

S-2,

-continued

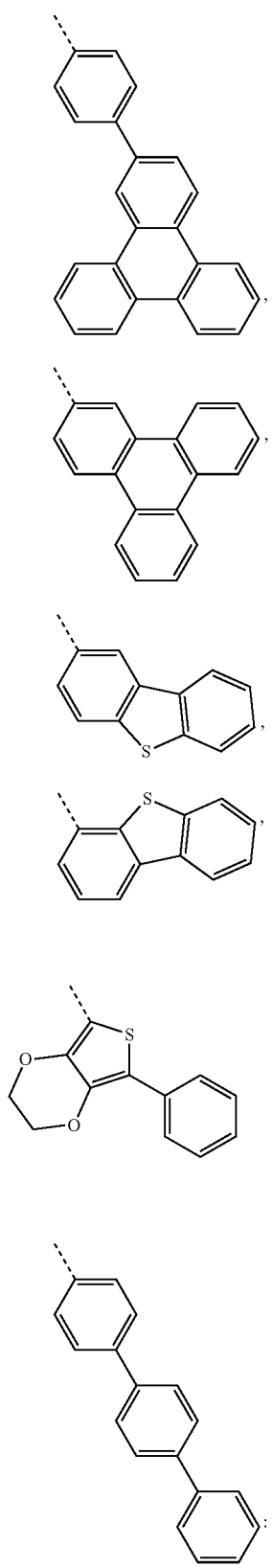

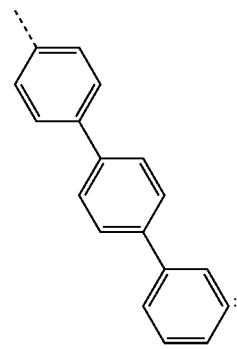

wherein the dotted line shows the point of attachment to an N atom of Formula I;

wherein at least one of $R_2$, $R_3$, and $R_4$ is selected from the group consisting of:

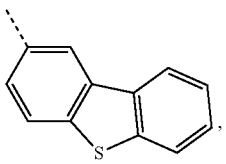
S-5

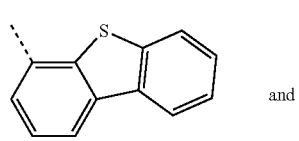
S-6 and

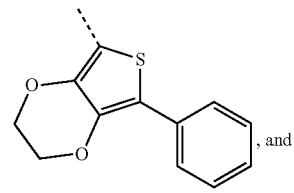
S-7, and wherein each of $R_1$, $R_2$, $R_3$ and $R_4$ may be further substituted with substituents that are not fused to $R_1$, $R_2$, $R_3$ and $R_4$.

2. The composition of matter of claim 1, wherein the part of the composition represented by Formula I is more specifically:

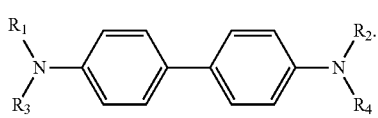
(Formula II)

3. The composition of matter of claim 1, wherein at least one of $R_2$, $R_3$, and $R_4$ is

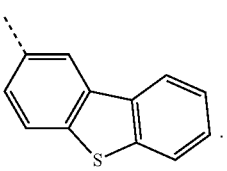
S-5

4. The composition of matter of claim 1, wherein at least one of $R_2$, $R_3$ and $R_4$ is

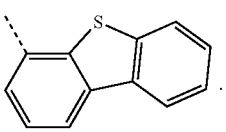
S-6

5. The composition of matter of claim 1, wherein both $R_1$ and $R_2$ are

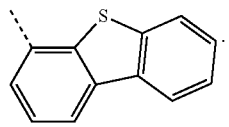

S-6

6. A composition of matter having the chemical structure:

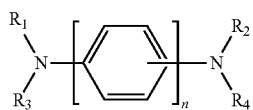

(Formula I)

wherein n is 1, 2, or 3, and the phenyl rings between the nitrogen atoms may be attached to each other and to the nitrogen atoms in a para or meta configuration independently selected for each attachment;

wherein each of $R_1$, $R_2$, $R_3$, and $R_4$ are independently selected from the group consisting of:

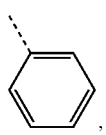

S-1

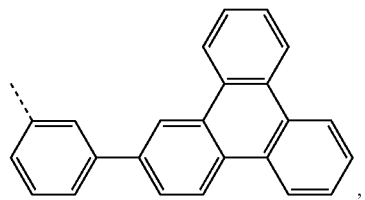

S-2

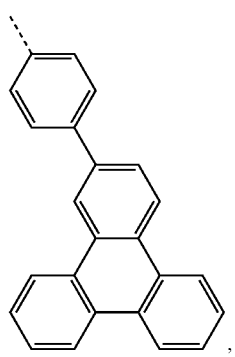

S-3

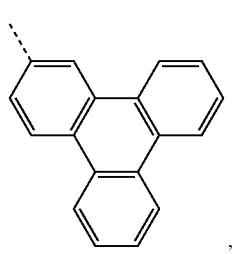

S-4

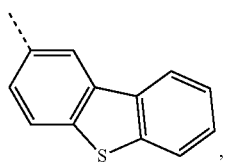

S-5

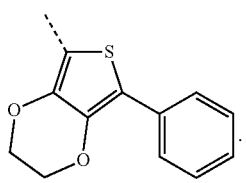

S-6

S-7 wherein the dotted line shows the point of attachment to an N atom of Formula I;

wherein at least one of $R_1$, $R_2$, $R_3$, and $R_4$ is

S-7 wherein each of $R_1$, $R_2$, $R_3$, and $R_4$ may be further substituted with substituents that are not fused to $R_1$, $R_2$, $R_3$, and $R_4$.

7. The composition of matter of claim 1, wherein at least one of $R_2$, $R_3$, and $R_4$ is selected from the group consisting of:

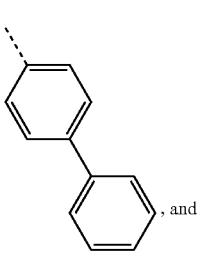

S-8

, and

-continued

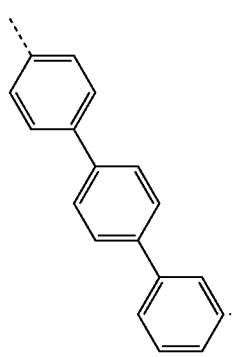

S-9

8. The composition of matter of claim 1, wherein $R_1$ is selected from the group consisting of:

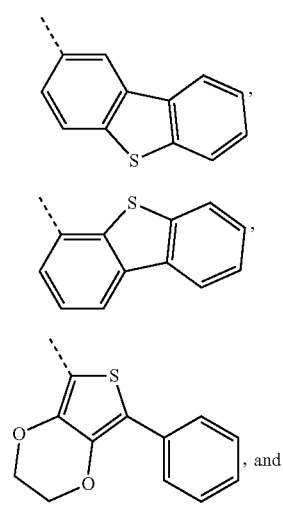

S-5

S-6

S-7

S-9 and each of $R_1$, $R_2$, $R_3$, and $R_4$ is independently selected from the group consisting of:

S-1

-continued

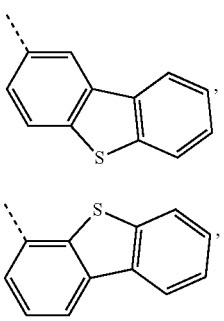

S-5

S-6

S-7

S-8

S-9 and there are no further substitutions to $R_1$, $R_2$, $R_3$, and $R_4$.

9. The composition of matter of claim 3, wherein the composition of matter has a structure selected from the group consisting of:

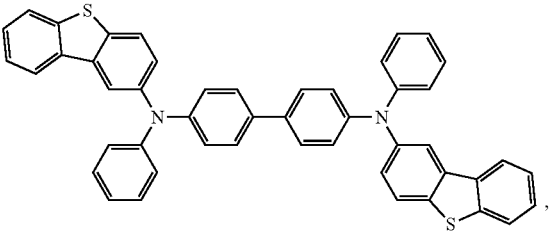

A-1

-continued
A-2
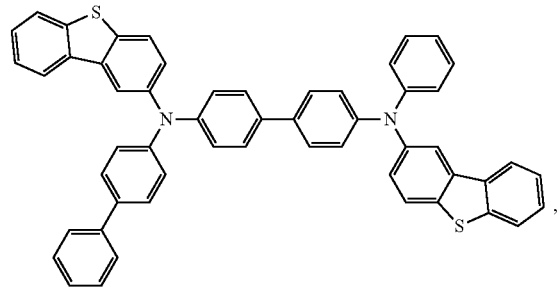
A-3
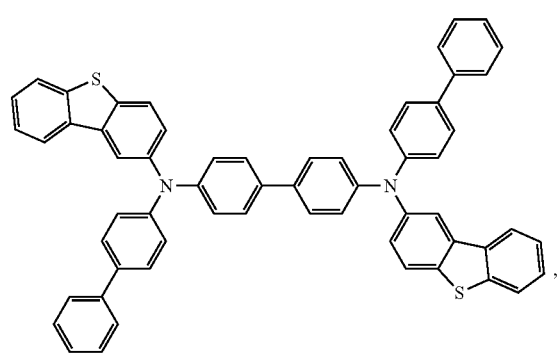
A-6
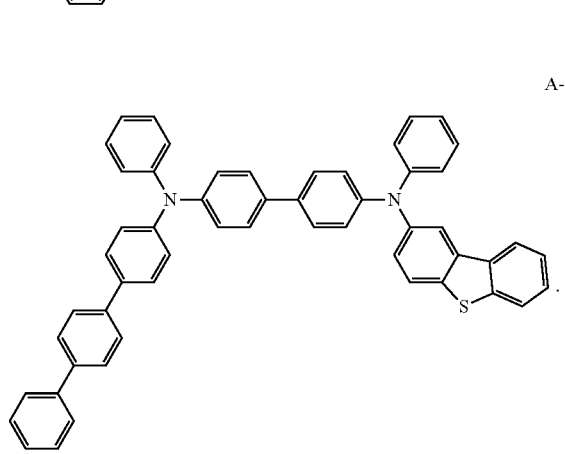
B-1
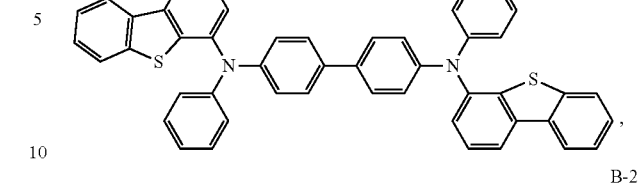
B-2
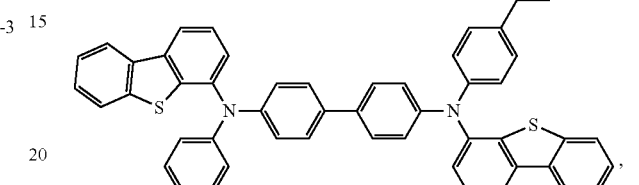
B-3
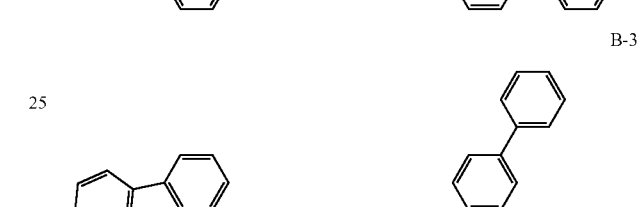
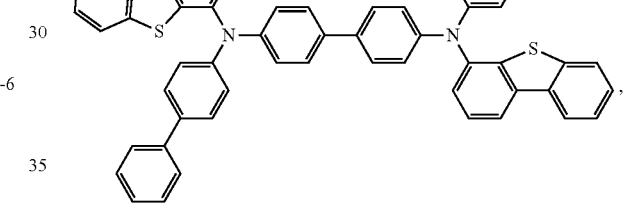
B-6
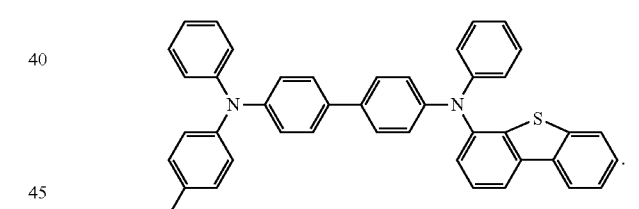
10. The composition of matter of claim 9, wherein the composition of matter has the structure:
A-1
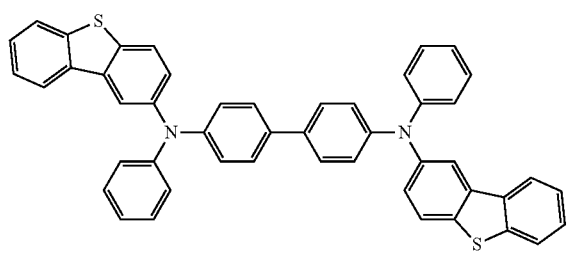
11. The composition of matter of claim 4, wherein the composition of matter has a structure selected from the group consisting of:
12. The composition of matter of claim 11, wherein the composition of matter has the structure:
B-1
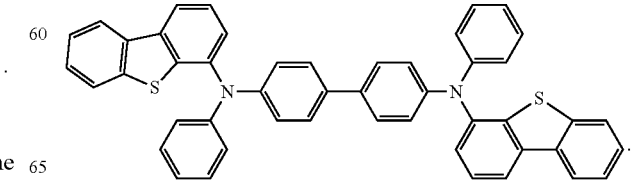

13. The composition of matter of claim 5, wherein the composition of matter has a structure selected from the group consisting of:
C-1
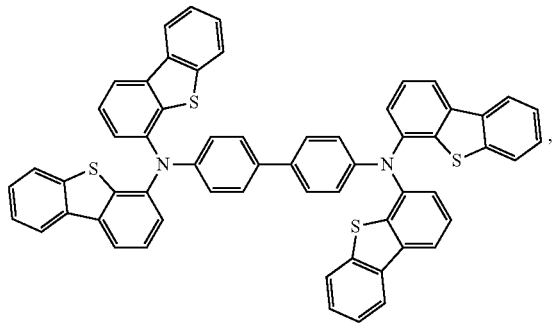
C-2
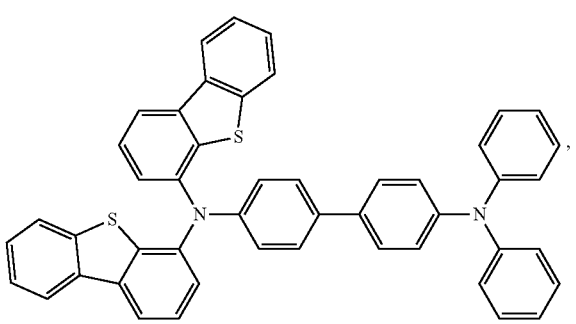
C-3
C-4
C-5
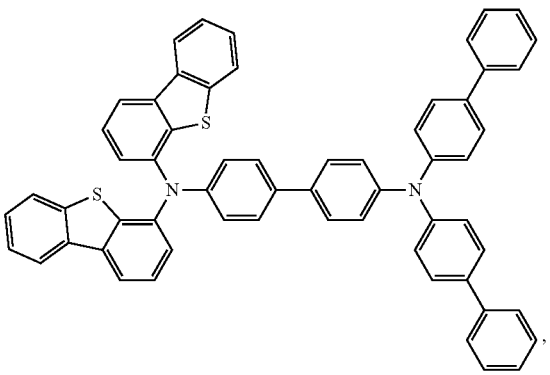
C-6
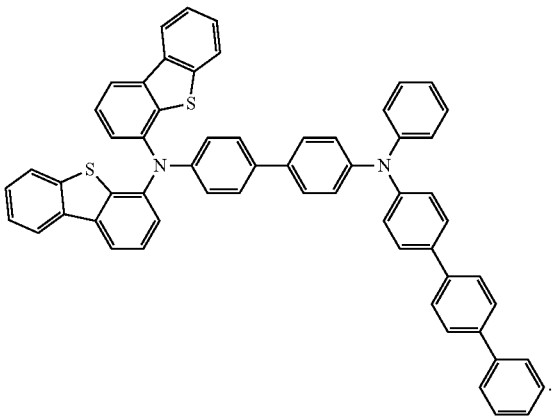
14. The composition of matter of claim 13, wherein the composition of matter has the structure:
C-1
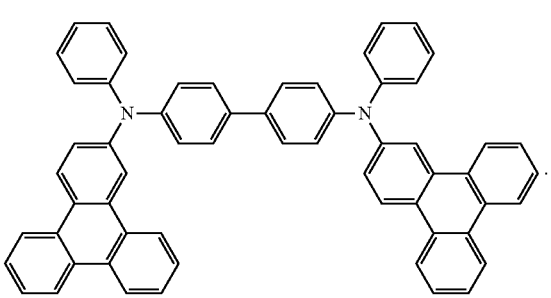
15. The composition of matter of claim 6, wherein the composition of matter has a structure selected from the group consisting of:

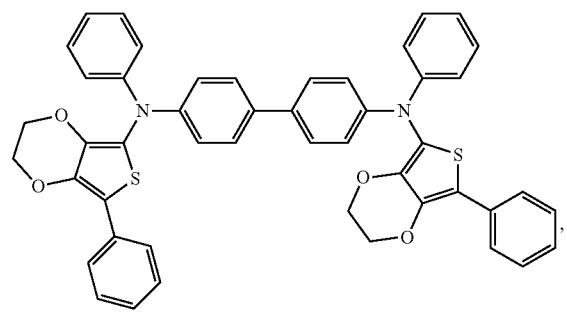
D-1

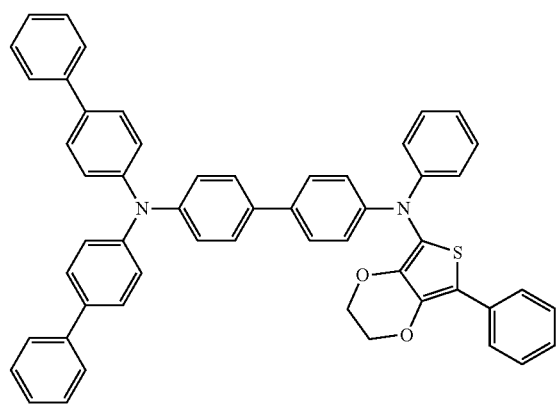
D-5

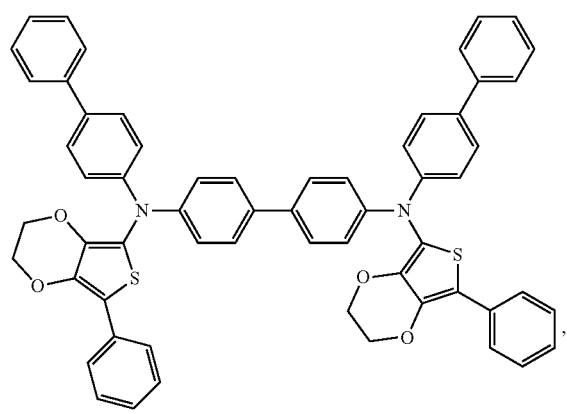
D-2

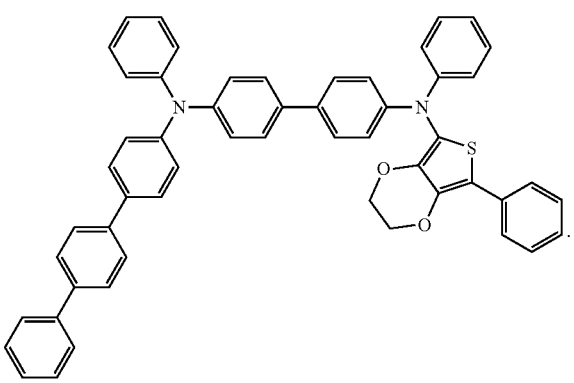
D-6

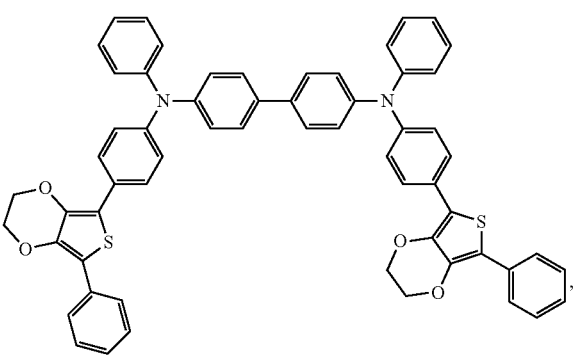
D-3

16. The composition of matter of claim 15, wherein the composition of matter has the structure:

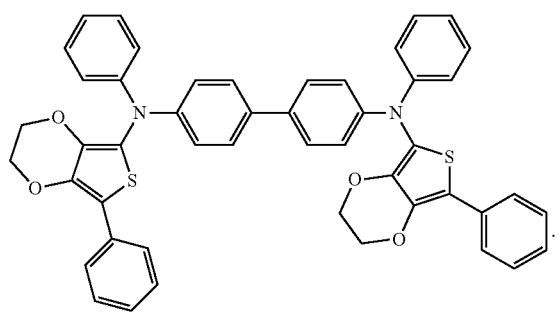
D-1

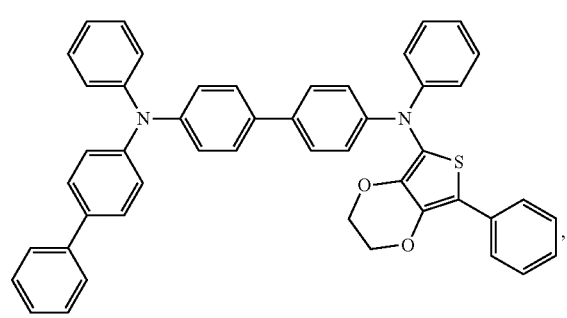
D-4

17. An organic light emitting device comprising:
an anode;
a cathode;
an organic emissive layer, disposed between the anode and the cathode, the organic emissive layer further comprising a host and a phosphorescent dopant,
an organic hole transport layer comprising a hole transport material, disposed between the organic emissive layer and the anode, and in direct contact with the organic emissive layer;

wherein the hole transport material has the structure:

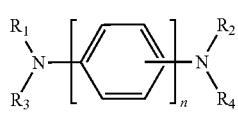
(Formula 1)

wherein n is 1, 2 or 3, and the phenyl rings between the nitrogen atoms may be attached to each other and to the nitrogen atoms in a para or meta configuration independently selected for each attachment;

wherein each of $R_2$, $R_3$ and $R_4$ are independently selected from the group consisting of:

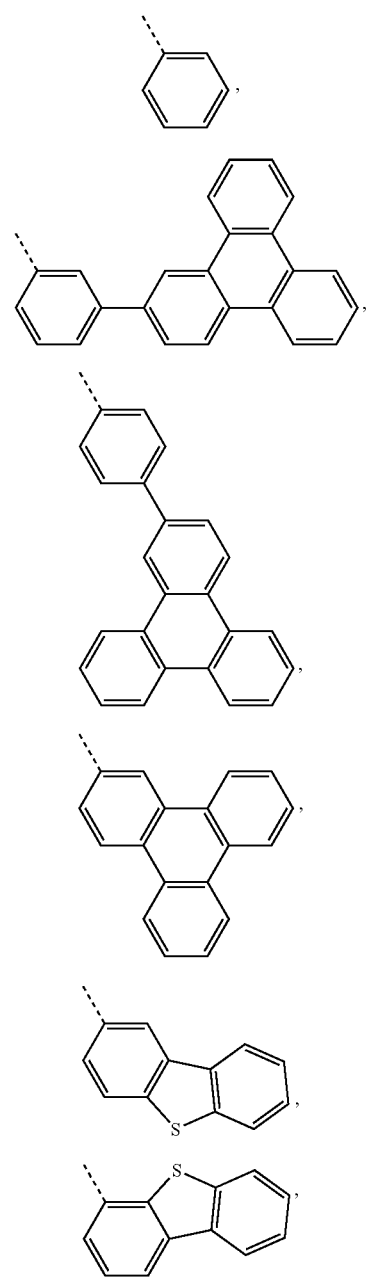

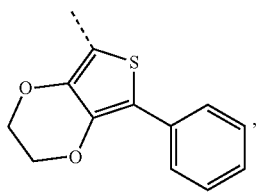
S-7

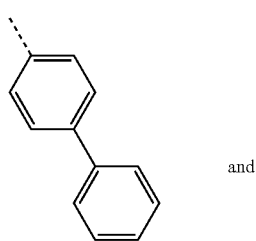
S-8
and

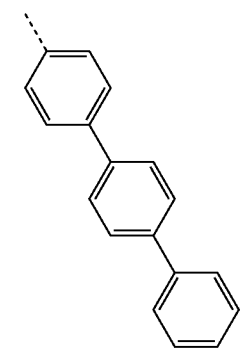
S-9 wherein $R_1$ is selected from the group consisting of:

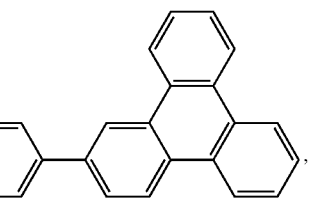
S-2

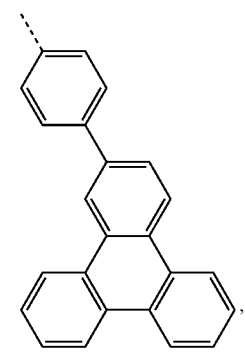
S-3

-continued
S-4
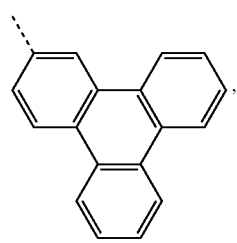
S-5
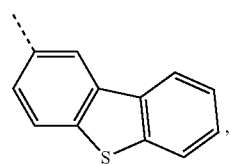
S-6
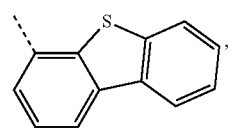
S-7
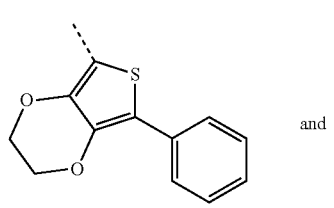
and
S-9
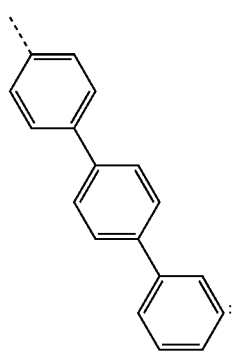
;
wherein the dotted line shows the point of attachment to an N atom of Formula I:
wherein at least one of $R_2$, $R_3$ and $R_4$ is selected from the group consisting of:
S-5
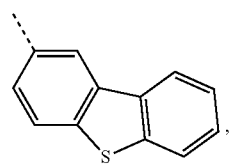
,
S-6
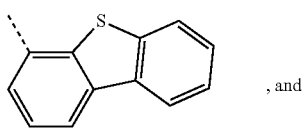
, and
-continued
S-7
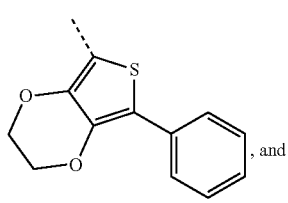
, and
wherein each of $R_1$, $R_2$, $R_3$ and $R_4$ may be further substituted with substituents that are not fused to $R_1$, $R_2$, $R_3$ and $R_4$,
S-2
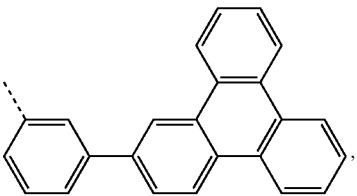
,
S-3
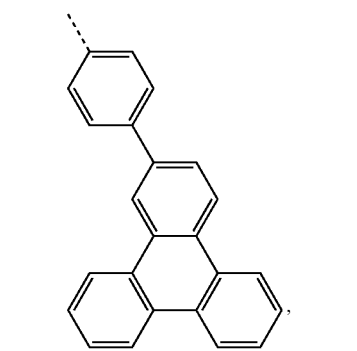
,
S-4
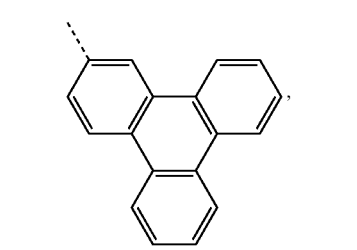
,
S-5
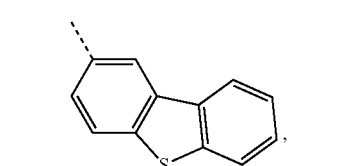
,
S-6
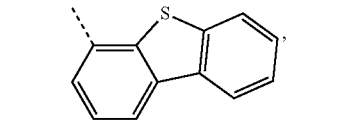
, -continued

S-7

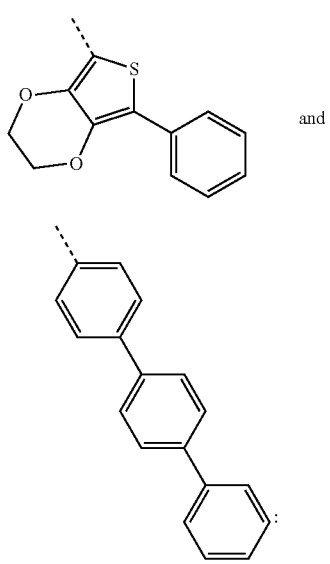

S-9 wherein the dotted line shows the point of attachment to an N atom of Formula I;
wherein at least one of $R_2$, $R_3$, and $R_4$ is selected from the group consisting of:

S-5

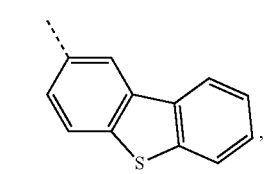

S-6

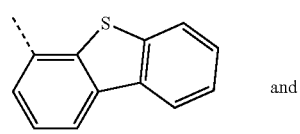

and

S-7

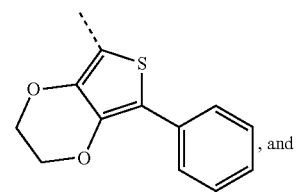

, and wherein each of $R_1$, $R_2$, $R_3$, and $R_4$ may be further substituted with substituents that are not fused to $R_1$, $R_2$, $R_3$, and $R_4$.

18. The device of claim 17, wherein the dopant is an organo-metallic iridium material.

19. The device of claim 17, wherein at least one of $R_2$, $R_3$, and $R_4$ is s-6

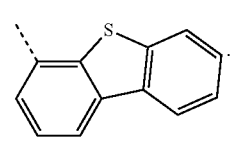

20. The device of claim 19, wherein the host is a compound comprising a triphenylene containing benzo-fused thiophene.

21. A consumer product, wherein the consumer product includes an organic light emitting device that further includes a composition of matter having the chemical structure:

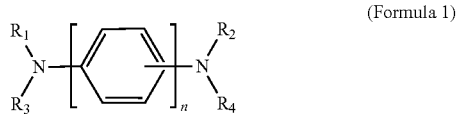

(Formula 1)

wherein n is 1, 2 or 3, and the phenyl rings between the nitrogen atoms may be attached to each other and to the nitrogen atoms in a para or meta configuration independently selected for each attachment;
wherein each of $R_2$, $R_3$ and $R_4$ are independently selected from the group consisting of:

S-1

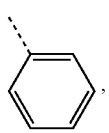

S-2

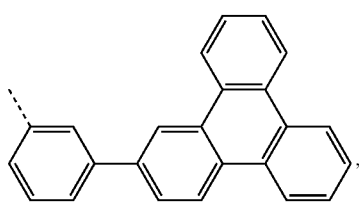

S-3

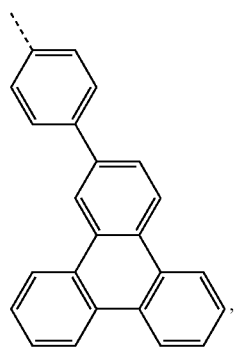

S-4

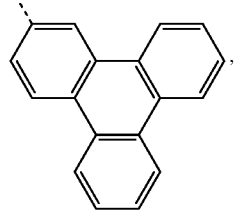

S-5

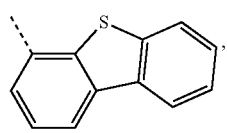
S-6,
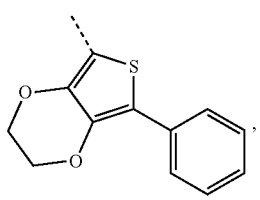
S-7,
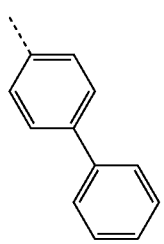
S-8
and
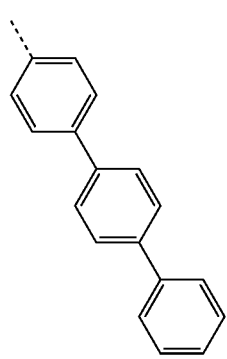
wherein R₁ is selected from the group consisting of:
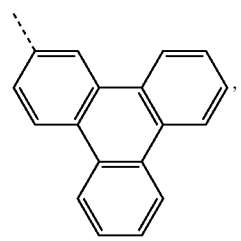
S-4,
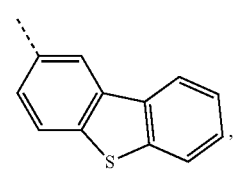
S-5,
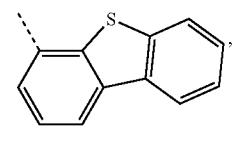
S-6,
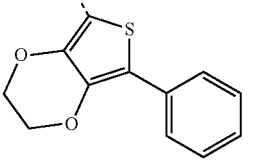
S-7
and
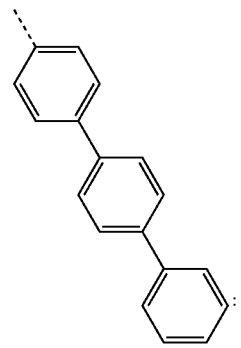
S-9
:
wherein the dotted line shows the point of attachment to an N atom of Formula I;
wherein at least one of R₂, R₃ and R₄ is selected from the group consisting of:
S-2
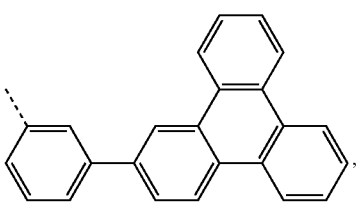
,
S-3
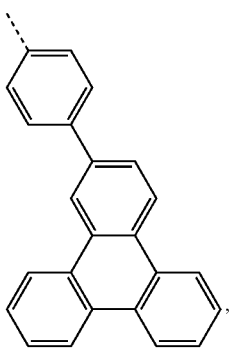
,
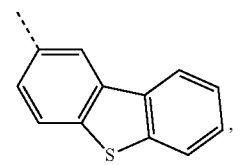
S-5,
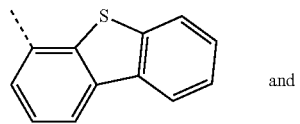
S-6
and

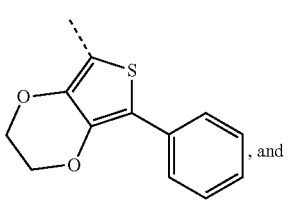, and
wherein each of $R_1$, $R_2$, $R_3$ and $R_4$ may be further substituted with substituents that are not fused to $R_1$, $R_2$, $R_3$ and $R_4$.
* * * * *